US011339375B2

(12) United States Patent
Schmitt et al.

(10) Patent No.: US 11,339,375 B2
(45) **Date of Patent: *May 24, 2022**

(54) PARAMYXOVIRUS VIRUS-LIKE PARTICLES AS PROTEIN DELIVERY VEHICLES

(71) Applicant: The Penn State Research Foundation, University Park, PA (US)

(72) Inventors: Anthony Paul Schmitt, State College, PA (US); Phuong Tieu Schmitt, State College, PA (US); Greeshma Vivekananda Ray, Cleveland, OH (US)

(73) Assignee: The Penn State Research Foundation, University Park, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/433,412

(22) Filed: Jun. 6, 2019

(65) Prior Publication Data

US 2019/0338253 A1 Nov. 7, 2019

Related U.S. Application Data

(63) Continuation of application No. 15/383,324, filed on Dec. 19, 2016, now Pat. No. 10,316,295.

(60) Provisional application No. 62/268,921, filed on Dec. 17, 2015.

(51) Int. Cl.

*C12N 7/00* (2006.01)
*C07K 14/005* (2006.01)
*C12N 9/02* (2006.01)
*C07K 14/81* (2006.01)
*C07K 16/10* (2006.01)

(52) U.S. Cl.

CPC .............. *C12N 7/00* (2013.01); *C07K 14/005* (2013.01); *C07K 14/8121* (2013.01); *C07K 16/1027* (2013.01); *C12N 9/0069* (2013.01); *C12N 9/0089* (2013.01); *C12Y 113/12005* (2013.01); *C12Y 115/01001* (2013.01); *C12N 2760/18022* (2013.01); *C12N 2760/18023* (2013.01); *C12N 2760/18034* (2013.01); *C12N 2760/18222* (2013.01); *C12N 2760/18223* (2013.01); *C12N 2760/18234* (2013.01); *C12N 2760/18252* (2013.01); *C12N 2760/18722* (2013.01); *C12N 2760/18723* (2013.01); *C12N 2760/18734* (2013.01)

(58) Field of Classification Search

None

See application file for complete search history.

(56) References Cited

U.S. PATENT DOCUMENTS

| | | | |
|---|---|---|---|
| 8,765,666 B2 | 7/2014 | Szolajska et al. |
| 2006/0216702 A1 | 9/2006 | Compans et al. |
| 2011/0097355 A1 | 4/2011 | Morrison |
| 2011/0250675 A1 | 10/2011 | Bennett |
| 2012/0087940 A1 | 4/2012 | Inoue et al. |

FOREIGN PATENT DOCUMENTS

| | | | |
|---|---|---|---|
| WO | 00/09157 A1 | 2/2000 |
| WO | 2008/061243 A2 | 5/2008 |

OTHER PUBLICATIONS

Coronel et al., Nucleocapsid Incorporation into Parainfluenza Virus is Regulated by Specific Interaction with Matrix Protein, 2001, Journal of Virology, vol. 75, No. 3, pp. 1117-1123.*

Tscherne, D.M., et al., An Enzymatic Virus-Like Particle Assay for Sensitive Detection of Virus Entry, Virol Methods, Feb. 2010, vol. 163, No. 2, pp. 1-15.

Tan, W.S., et al., Solubility, Immunogenicity and Physical Properties of the Nucleocapsid Protein of Nipah Virus Produced in *Escherichia coli*, J. Med., Virol., 2004, vol. 73, pp. 105-112.

Schmitt, A.P., et al., Requirements for Budding of Paramyxovirus Simian Virus 5 Virus-Like Particles, Journal of Virology, Apr. 2002, vol. 76, No. 8, pp. 3952-3964.

Li, M., et al., Mumps Virus Matrix, Fusion, and Nucleocapsid Proteins Cooperate for Efficient Production of Virus-Like Particles, Journal of Virology, May 13, 2009, vol. 83, No. 14, pp. 7261-7272.

Patch, J.R., et al., Quantitative analysis of Nipah virus proteins released as virus-like particles reveals central role for the matrix protein, Virology Journal, Jan. 4, 2007, vol. 4, No. 1, pp. 1-14.

Harrison, M.S., et al., Paramyxovirus assembly and budding: Building particles that transmit infections, The International Journal of Biochemistry and Cell Biology, Apr. 14, 2010, vol. 42, pp. 1416-1429.

Schmitt, P.T., et al., The C-Terminal End of Parainfluenza Virus 5 NP Protein is Important for Virus-Like Particle Production and M-NP Protein Interaction, Journal of Virology, Oct. 13, 2010, vol. 84, No. 24, pp. 12810-12823.

(Continued)

*Primary Examiner* — Benjamin P Blumel

(74) *Attorney, Agent, or Firm* — Hodgson Russ LLP

(57) ABSTRACT

Provided are modified virus-like particles (VLPs) of paramyxoviruses, compositions containing them, methods of using the VLPs for delivery of any particular protein of interest to any of a variety of cells, kits that contain expression vectors for making, using and detecting VLPs, and methods for screening for anti-viral compounds using the VLPs. The modified VLPs contain a contiguous recombinant polypeptide that contains i) all or a segment of a C-terminal domain of a paramyxovirus nucleocapsid protein and ii) a polypeptide sequence of a distinct protein. Non-covalent complexes of paramyxovirus M protein and fusion proteins that contain a C-terminal domain of a paramyxovirus nucleocapsid protein and a polypeptide sequence of a distinct protein are provided, as are non-covalent complexes of cells, and cell receptors, with modified VLPs.

5 Claims, 11 Drawing Sheets

Specification includes a Sequence Listing.

(56) References Cited

OTHER PUBLICATIONS

Iwasaki, M., et al., The Matrix Protein of Measles Virus Regulates Viral RNA Synthesis and Assembly by Interacting with the Nucleocapsid Protein, Journal of Virology, Aug. 5, 2009, vol. 83, No. 20, pp. 10374-10383.

Kaczmarczyk, S.J., et al., Protein delivery using engineered virus-like particles, Proc. of the Natl. Acad. of Sci. U.S.A., Oct. 11, 2011, vol. 108, No. 41, pp. 16998-17003.

Capul, A.A., and De La Torre, J.C., A cell-based luciferase assay amenable to high-throughput screening of inhibitors of arenavirus budding, Virology, Oct. 16, 20018, vol. 382, No. 1, pp. 107-114.

Wolf, M.C., et al., A catalytically and genetically optimized beta-lactamase-matrix based assay for sensitive, specific, and higher throughput analysis of native henipavirus entry characteristics, Virology Journal, Jul. 31, 2009, vol. 6, No. 119, pp. 1-11.

Pantua, H.D., et al., Requirements for the Assembly and Release of Newcastle Disease Virus-Like Particles, J. Virol. Nov. 2006, vol. 80, No. 22, pp. 11062-11073.

* cited by examiner

Viral strategy for genome packaging via M-NP interactions

Manipulating genome packaging interactions to package a foreign protein into budding particles

A

SEQ ID NO:14

```
RLuc-NiV N15            . . . L K P A Q N D L D F V R A D V *
RLuc-NiV N15 L518A            A . . . . . . . . . . . . . . *
RLuc-NiV N15 K519A            . A . . . . . . . . . . . . . *
RLuc-NiV N15 P520A            . . A . . . . . . . . . . . . *
RLuc-NiV N15 Q522A            . . . . A . . . . . . . . . . *
RLuc-NiV N15 N523A            . . . . . A . . . . . . . . . *
RLuc-NiV N15 D524A            . . . . . . A . . . . . . . . *
RLuc-NiV N15 L525A            . . . . . . . A . . . . . . . *
RLuc-NiV N15 D526A            . . . . . . . . A . . . . . . *
RLuc-NiV N15 F527A            . . . . . . . . . A . . . . . *
RLuc-NiV N15 V528A            . . . . . . . . . . A . . . . *
RLuc-NiV N15 R529A            . . . . . . . . . . . A . . . *
RLuc-NiV N15 D531A            . . . . . . . . . . . . . A . *
RLuc-NiV N15 V532A            . . . . . . . . . . . . . . A *
```

B

[Bar chart showing Relative efficiency of luciferase incorporation for RLuc, RLuc-N15, and N15 alanine mutants L518A, K519A, P520A, Q522A, N523A, D524A, L525A, D526A, F527A, V528A, R529A, D531A, V532A]

...QNAAVGAPIHTDDLNAALGDLDI PIV5 SEQ ID NO:1
...EHGNTFPNNPNQNAQSQVGDWDE MuV SEQ ID NO:2
...DDDANDATDGNDISLELVGDFDS HPIV2 SEQ ID NO:3

...SEKKNNQDLKPAQNDLDFVRADV NiV SEQ ID NO:4
...GTPQSGPPPTPGPSQDNDTDWGY NDV SEQ ID NO:5
...GRNNGVDHDEDDDTAAVAGVGGI SeV SEQ ID NO:6
...GILEEQGSDTDTPRVYNDRDLLD MeV SEQ ID NO:7
...DLTAEELEAIKHQLNPKDNDVEL HRSV SEQ ID NO:8

|  | Membrane-bound | Membrane-free |
|---|---|---|
| PIV5 M | | |
| PIV5 NP | | |
| PIV5 NP | | |
| PIV5 M | | |
| PIV5 NP | | Mumps virus M and PIV5 NP proteins are incompatible |
| MuV M | | |
| PIV5 NP | | Nipah virus M and PIV5 NP proteins are compatible |
| NiV M | | |
| PIV5 NP L507W | | Changing DLD to DWD allowed PIV5 NP to bind mumps virus M |
| MuV M | | |
| PIV5 NP L507W | | Changing DLD to DWD did not impair PIV5 NP binding to PIV5 M |
| PIV5 M | | |

PARAMYXOVIRUS VIRUS-LIKE PARTICLES AS PROTEIN DELIVERY VEHICLES

CROSS REFERENCE TO RELATED APPLICATIONS

This application is a continuation of U.S. patent application Ser. No. 15/383,324, filed Dec. 19, 2016, which claims priority to U.S. Provisional application No. 62/268,921, filed Dec. 17, 2015, the disclosures of each of which are incorporated herein by reference.

STATEMENT REGARDING FEDERALLY SPONSORED RESEARCH

This invention was made with government support under contract no. AI070925 awarded by the National Institutes of Health, and contract nos. PEN04215 and PEN04497 awarded by the United States Department of Agriculture. The government has certain rights in the invention.

BACKGROUND OF THE DISCLOSURE

There is an ongoing and unmet need for compositions and methods that are useful for protein delivery to a variety of cell types for a variety of purposes. The present disclosure pertains to this need.

SUMMARY OF THE DISCLOSURE

The present disclosure relates to modified virus-like particles of paramyxoviruses, compositions comprising them, and methods of using them for delivery of any particular protein of interest to any of a variety of cells. The cells include but are not necessarily limited to mammalian cells. Generally, the disclosure involves introducing into a cell a foreign protein as an engineered component of a paramyxovirus virus like particle (VLP). The compositions, methods and kits accordingly pertain to modified VLPs that contain a contiguous recombinant polypeptide comprising i) all or a segment of a C-terminal domain of a paramyxovirus nucleocapsid protein and ii) a polypeptide sequence of a distinct protein. Paramyxovirus nucleocapsid proteins are referred to as the “N” protein, but it will be recognized that in certain cases the nucleocapsid protein can be what may be referred to in the art for any particular paramyxovirus as the “NP” protein. The N protein can have an amino acid sequence that is the same as a segment of any naturally occurring N protein, or the sequence of the N protein can be modified, such as to provide for enhanced function. The type of paramyxovirus N protein C-terminal sequence that is used or is modified for use in embodiments of this disclosure is not particularly limited. In non-limiting embodiments, the N protein C-terminal sequence that is used and/or modified is from PIV5, hPIV2, Nipah virus, Hendra virus, mumps virus (MuV), measles virus (MeV), Newcastle disease virus (NDV), Sendai virus (SeV), respiratory syncytial virus (RSV), and human metapneumovirus (hMPV). Non-limiting embodiments of the disclosure are provided using PIV5 VLPs, Nipah VLPs, and mumps VLPs. In certain embodiments, C-terminal segment of the N protein that is present in a fusion with a distinct protein is at least 10 amino acids in length, and can be from 0-120 amino acids in length, and the fusion protein may comprise one or more C-terminal segments, and may comprise any suitable linker or linkers. As will be illustrated in the detailed description and examples, in certain embodiments, the C-terminal segment of the N protein can comprise a DLD or DWD amino acid motif. In certain embodiments, the disclosure includes complexes that comprise non-covalent associations of paramyxovirus M protein, and a fusion protein of this disclosure, wherein the fusion protein comprises a foreign protein and a paramyxovirus N protein C-terminal sequence. Such complexes may be present in VLPs of this disclosure. In embodiments, non-covalent associations of cells and modified VLPs are provided. In embodiments, non-covalent associations of VLPs of this disclosure that are formed between the VLPs and sialic acid are provided. In embodiments, non-covalent associations of VLPs of this disclosure with Ephrin B2, Ephrin B3, SLAM and/or Nectin4 receptors are provided. In certain embodiments, complexes comprising antibodies and VLPs of this disclosure are provided.

Expression vectors encoding the fusion proteins are provided, as are cells that contain such expression vectors. Methods of making the VLPs are included, as are isolated and/or purified VLP preparations, wherein the VLPs have been separated from cells, including but not necessarily limited to VLP producer cells. It will be recognized that the VLPs can be made by producing any one or any combination of VLP components recombinantly, i.e., by expression from an expression vector. In embodiments, the VLPs are produced using one or more expression vectors in cells, wherein the cells express at least: paramyxovirus M, N or NP, F and Attachment proteins, non-limiting examples or which are described herein.

In certain implementations the disclosure comprises compositions comprising the VLPs, which may be provided as pharmaceutical compositions. In embodiments the disclosure comprises administering the VLPs and/or compositions comprising them to cells, and/or to individuals in need thereof. The administration results in a foreign protein that is present in a fusion protein of the VLPs being introduced to the cell.

Methods of screening for anti-viral compounds are provided. These methods generally comprise determining whether one or more test agents can inhibit one or more steps of viral infection and/or reproduction by mixing modified VLPs of this disclosure, cells and test agents and determining whether or not the test agents inhibit any of the one or more steps.

Also provided are kits. The kits can comprise an expression vector encoding a segment of a C-terminal domain of a paramyxovirus nucleocapsid protein in proximity to a cloning site configured so that a polynucleotide encoding a distinct polypeptide can be introduced into the cloning site. This configuration results in the capability of the expression vector to express the segment of the C-terminal domain and the distinct polypeptide in a contiguous fusion protein, which may be incorporated into VLPs. The kits can comprise at least one additional expression vector encoding at least one additional VLP component, wherein the at least one additional component is selected from a viral matrix protein, a viral attachment glycoprotein, and a viral fusion glycoprotein. Or, a single expression vector can be adapted to express more than one of these proteins. In embodiments, a kit also comprises an antibody or antigen binding fragment thereof, wherein the antibody or antigen binding fragment thereof binds with specificity to the C-terminal domain of the N-protein that is incorporated into a fusion protein with the foreign protein, as described herein.

BRIEF DESCRIPTION OF THE FIGURES

(FIG. 2A) Illustration of *Renilla* luciferase proteins appended with residues derived from PIV5 NP protein. 5, 10, 15, 30, or 50 amino acid residues from the C-terminal end of PIV5 NP protein were transplanted onto the C-terminal end of *Renilla* luciferase. (FIG. 2B) 293T cells were transfected to produce PIV5 M and HN proteins together with the indicated *Renilla* luciferase-NP fusions. VLPs released into the culture supernatants were purified by centrifugation through sucrose cushions followed by flotation on sucrose gradients. Viral proteins from cell lysate and purified VLP fractions were detected by immunoblotting. RLuc-NP15, -NP30, and -NP50 succeeded in triggering VLP release, and were recovered in the VLPs to a much greater extent than unmodified RLuc. From this, it is concluded that 15 C-terminal residues of PIV5 NP protein are sufficient to direct a foreign protein into budding PIV5 particles.

(FIG. 5A) Illustration of *Renilla* luciferase proteins appended with residues derived from Nipah virus N protein. 5, 10, 15, 30, or 50 amino acid residues from the C-terminal end of Nipah virus N protein were transplanted onto the C-terminal end of *Renilla* luciferase. (FIG. 5B) 293T cells were transfected to produce Nipah virus M protein together with the indicated *Renilla* luciferase-N fusions. VLPs released into the culture supernatants were purified by centrifugation through sucrose cushions followed by flotation on sucrose gradients. Viral proteins from cell lysate and purified VLP fractions were detected by immunoblotting. RLuc-N10, -N15, -N30, and -N50 were recovered in the VLPs to a much greater extent than unmodified RLuc. From this, it is concluded that 10 C-terminal residues of Nipah virus N protein are sufficient to direct a foreign protein into budding Nipah VLPs.

(FIG. 6A) Schematic illustrating variations on RLuc-N15, generated by site-directed mutagenesis. Only the 15 residues derived from Nipah virus N protein are shown. (FIG. 6B) 293T cells were transfected to produce Nipah virus M protein together with the indicated variants of RLuc-N15. VLPs released into the culture supernatants were purified by centrifugation through sucrose cushions followed by flotation on sucrose gradients. Viral proteins from cell lysate and purified VLP fractions were detected by immunoblotting. The asterisk denotes the position of RLuc-N15 variants that could be detected using a polyclonal antibody raised against Nipah virus N protein. (FIG. 6C) Three independent experiments were performed as described for panel B, and relative efficiencies of luciferase incorporation into VLPs were calculated as the amount of luciferase detected in VLPs divided by the amount of M protein detected in VLPs, normalized to the value obtained with RLuc-N15. Error bars indicate standard deviations. *$p<0.05$; **$p<0.005$.

DESCRIPTION OF THE DISCLOSURE

Unless defined otherwise herein, all technical and scientific terms used in this disclosure have the same meaning as commonly understood by one of ordinary skill in the art to which this disclosure pertains.

Every numerical range given throughout this specification includes its upper and lower values, as well as every narrower numerical range that falls within it, as if such narrower numerical ranges were all expressly written herein.

The present disclosure relates to modified virus-like particles of paramyxoviruses, compositions comprising them, and methods of using them.

Paramyxoviruses are responsible for a wide range of diseases that affect both humans and animals. Paramyxovirus pathogens include measles virus, mumps virus, human respiratory syncytial virus, and the zoonotic paramyxoviruses Nipah virus and Hendra virus. Infectivity of paramyxovirus particles depends on matrix-nucleocapsid protein interactions which enable efficient packaging of encapsidated viral RNA genomes into budding virions.

Figure 1:
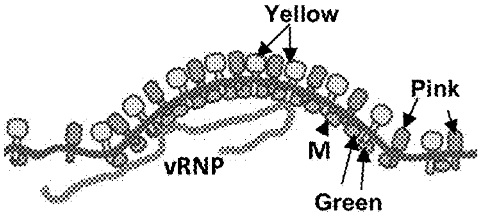
FIG. 1. Overview of an embodiment of the disclosure. The left panel depicts the incorporation of a viral ribonucleoprotein (vRNP) into a paramyxovirus particle as the particle buds from an infected cell plasma membrane. Incorporation is accomplished via an interaction between the nucleocapsid component of the vRNP and the viral matrix (M) protein, shown in green. Also present at the budding site are the viral attachment and fusion transmembrane glycoproteins, shown in yellow and pink. The right panel illustrates the strategy used to manipulate genome packaging interactions to package a foreign protein into paramyxovirus virus-like particles (VLPs). A foreign protein (in this case *Renilla* luciferase, represented by a light bulb), has been modified so that 15 amino acid residues of a paramyxovirus NP sequence has been attached to its C-terminal end. It now binds to M protein and is incorporated into budding particles via the same interaction that drives incorporation of vRNPs into paramyxovirus virions.
Figure 1:
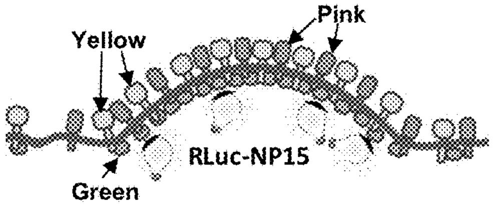
Figure 2:
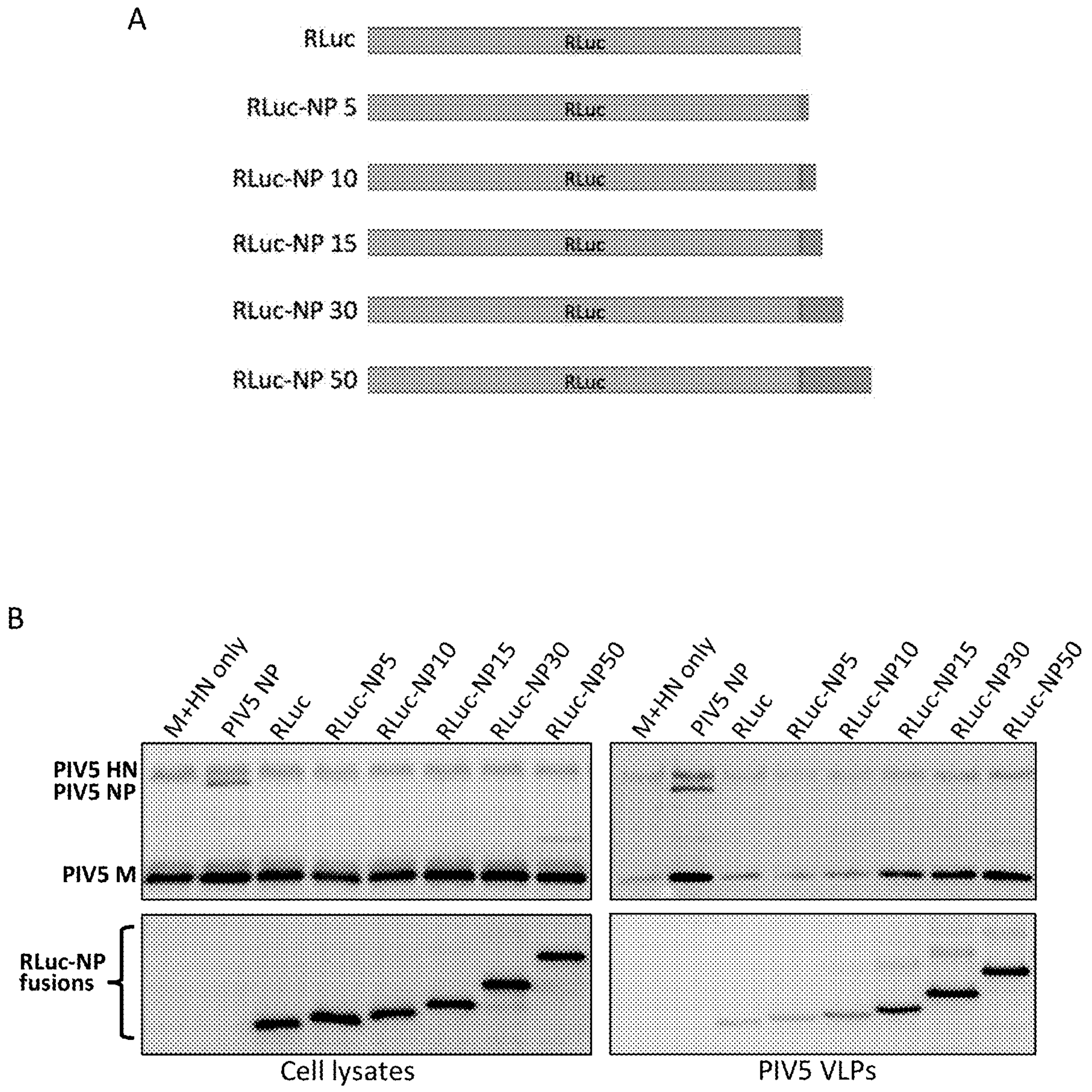
FIG. 2. Data showing manipulation of paramyxovirus genome packaging interactions to direct *Renilla* luciferase into PIV5 VLPs.

Paramyxovirus infections are spread via particles, which bud from plasma membranes of infected cells. Formation of these particles is driven by the viral matrix (M) proteins which can self-assemble to form ordered yet flexible arrays that likely play key roles in generating the membrane curvature required for budding. M proteins also organize the particle assembly process by interacting with the viral glycoproteins via their cytoplasmic tails, and also with the viral ribonucleoprotein (vRNP) complexes via the nucleocapsid (N or NP) proteins. These interactions bring together and concentrate all of the viral structural components onto specific sites underlying infected cell plasma membranes (as depicted in the left-hand panel of FIG. 1), enabling infectious virions to subsequently bud from these locations.

For many paramyxoviruses, expression of M protein in the absence of any other viral components is sufficient to induce the assembly and release of virus-like particles (VLPs) from transfected cells. M proteins of Sendai virus, measles virus, Nipah virus, Hendra virus, Newcastle disease virus, and human parainfluenza virus 1 are all capable of directing VLP production and release from transfected cells when expressed alone. In these cases, additional viral components including the viral glycoproteins and the nucleocapsid-like structures that form upon expression of paramyxovirus N/NP proteins can be efficiently packaged into the VLPs if they are co-expressed along with the M proteins (Harrison M S, Sakaguchi T, Schmitt A P. 2010. Paramyxovirus assembly and budding: building particles that transmit infections. Int. J. Biochem. Cell. Biol. 42:1416-1429.) For other paramyxoviruses, including mumps virus (Li M, Schmitt P T, Li Z, McCrory T S, He B, Schmitt A P. 2009. Mumps virus matrix, fusion, and nucleocapsid proteins cooperate for efficient production of virus-like particles. J. Virol. 83:7261-7272) and parainfluenza virus 5 (PIV5) (Schmitt A P, Leser G P, Waning D L, Lamb R A. 2002. Requirements for budding of paramyxovirus simian virus 5 virus-like particles. J. Virol. 76:3952-3964), the viral M proteins do not induce significant VLP production when expressed alone in transfected cells. In these cases, co-expression of M proteins together with viral glycoproteins and NP proteins is necessary for VLP production to occur. Such an arrangement could in theory provide a benefit to viruses by preventing the release of empty virions that lack vRNPs.

Paramyxovirus N/NP proteins function to bind and encapsidate viral genomic and antigenomic RNAs, forming helical nucleocapsid structures that serve as templates for the viral polymerase (Ruigrok R W H, Crépin T, Kolakofsky D. 2011. Nucleoproteins and nucleocapsids of negative-strand RNA viruses. Curr Opin Microbiol 14:504-510). Encapsidation, which is directed by the RNA-binding, N-terminal core regions of the N/NP proteins, also protects viral RNAs from RNase digestion and impairs recognition of viral RNAs by host innate immune responses. The C-terminal tail regions of paramyxovirus N/NP proteins are dispensable for RNA binding and instead function to direct interactions with a variety of viral and host proteins including viral M proteins and viral P proteins, although in some cases P protein binding and polymerase docking can instead be mediated by the N-terminal core region of N.

Interactions between matrix and nucleocapsid proteins of negative-strand RNA viruses are universally important for generation of infectious, genome-containing virus particles, but the details of these interactions are poorly understood. Studies with measles virus have defined a region very close to the C-terminal end of N protein that is necessary for M protein binding (Iwasaki M, Takeda M, Shirogane Y, Nakatsu Y, Nakamura T, Yanagi Y. 2009. The matrix protein of measles virus regulates viral RNA synthesis and assembly by interacting with the nucleocapsid protein. J. Virol. 83:10374-10383). For PIV5, the sequence DLD near the C-terminal end of NP protein is believed to be important for its virus assembly functions (Schmitt P T, Ray G, Schmitt A P. 2010. The C-terminal end of parainfluenza virus 5 NP protein is important for virus-like particle production and M-NP protein interaction. J. Virol. 84:12810-12823). Mutations to DLD abolished particle formation function and disrupted M-NP interaction. In view of these previous observations which provide an incomplete description of viral packaging we attempted to determine how viruses naturally package their contents into particles during an infection. However, during our analysis, we unexpectedly discovered that transplanting a region of the C-terminal end of PIV5 NP to an unrelated protein causes the unrelated protein to bind M and to consequently be packaged into virus-like particles. An illustration and data demonstrating this process are presented in FIGS. 1 through 4 and is discussed in greater detail below. The data presented in this disclosure demonstrate that a 15 residue-long, DLD-containing sequences derived from either the PIV5 or Nipah virus nucleocapsid protein C-terminal ends are sufficient to direct packaging of foreign proteins, such as *Renilla* luciferase, into budding VLPs. Mumps virus NP protein harbors DWD in place of the DLD sequence found in PIV5 NP protein, and consequently, PIV5 NP protein is incompatible with mumps virus M protein. A single amino acid change converting DLD to DWD within PIV5 NP protein induced compatibility between these proteins and allowed efficient production of mumps VLPs. These data support a model in which paramyxoviruses share an overall common strategy for directing M-NP interactions, but with variations contained within DLD-like sequences that play key roles in defining M/NP protein compatibilities, and lead to various embodiments of this disclosure, as follows.

In one aspect the disclosure relates to recombinant proteins comprising a segment of a paramyxovirus nucleocapsid protein and some or all of a distinct protein, i.e., some or all of a non-paramyxovirus nucleocapsid protein, also referred to herein as a "foreign protein." The foreign protein is thus a protein that is distinct from the N protein (but may nevertheless be present in a contiguous recombinant polypeptide that comprises a segment of the N protein). In general, the segment of the paramyxovirus nucleocapsid protein comprises or consists of a segment of the C-terminal portion of the nucleocapsid protein, characteristics and specific examples of which are described below. The disclosure includes all polynucleotide and amino acid sequences described herein, and every polynucleotide sequence referred to herein includes its complementary DNA sequence, and also includes the RNA equivalents thereof to the extent an RNA sequence is not given. Every DNA and RNA sequence encoding polypeptides disclosed herein is encompassed by this disclosure, including but not limited to sequences encoding all recombinant proteins that comprise a segment of a paramyxovirus nucleocapsid protein, as described further below. As will be recognized by those skilled in the art, paramyxovirus nucleocapsid proteins may be referred to as the "N" or "NP" protein, and for convenience are each referred to herein from time to time as the N protein. In embodiments, the disclosure comprises a complex between a contiguous recombinant protein of this disclosure that comprises an N protein segment and a distinct, foreign protein segment, wherein the contiguous recombinant protein is in a physical association with a paramyxovirus M protein. The physical association may be non-covalent. Thus, in embodiments, covalent linkages of an M protein (or equivalent thereof) with fusion proteins of this disclosure can be excluded from the invention.

The disclosure also includes complexes comprising the modified VLPs of this disclosure and cells, wherein the complex is formed between a membrane-bound receptor on target cells and a trans-membrane attachment glycoprotein of the modified VLPs. Such interactions may also be non-covalent. In this regard, it is known in the art that paramyxoviruses that have HN proteins use sialic acid as the cellular receptor. For example, in specific and non-limiting embodiments, PIV5, mumps, hPIV2, Newcastle disease, and Sendai viruses attach to sialic acid. Nipah and Hendra viruses use Ephrin B2 and Ephrin B3 as receptors, and Measles virus uses SLAM and Nectin4 as receptors. Thus non-covalent complexes of VLPs of this disclosure with all such cellular receptor moieties are encompassed. In certain embodiments, VLPs of this disclosure comprise a set of proteins, in addition to a cell-derived envelope. The following table provides accession numbers for representative and non-limiting embodiments of VLP components, along with the accession number of the virus' particular Matrix (M) gene, its Nucleocapsid (N or NP) gene, its Fusion (F) gene, and its Attachment gene (HN, H, or G):

| Virus | Matrix (M) sequence ID | Nucleocapsid (N or NP) sequence ID | Fusion (F) sequence ID | Attachment name | Attachment sequence ID |
|---|---|---|---|---|---|
| PIV5 (parainfluenza virus 5) | AAC95514.1 | AAC95511.1 | AAC95515.1 | HN | AAC95517.1 |
| mumps virus | AEI98828.1 | AEI98825.1 | AEI98829.1 | HN | AEI98831.1 |
| Nipah virus | AAF73379.1 | AAF73377.1 | AAK29087.1 | G | AAK29088.1 |
| human parainfluenza virus type 2 (hPIV2) | CAA40785.1 | CAA40783.1 | CAA40786.1 | HN | CAA40787.1 |
| measles virus | BAA34980.1 | BAA34977.1 | BAA34981.1 | H | BAA34982.1 |
| Sendai virus | AAB06280.1 | AAB06278.1 | AAB06281.1 | HN | AAB06282.1 |
| Newcastle disease virus | X04687.1 | AF064091.1 | X04719.1 | HN | X04355.1 |
| Hendra virus | AAC83191.2 | AAC83187.1 | AAC83192.2 | G | AAC83193.2 |
| Human respiratory syncytial virus (HRSV) | AEO45906.1 | AEO45904.1 | AEO45909.1 | G | AEO45908.1 |
| Human metapneumovirus | ACJ70105.1 | ACJ70103.1 | ACJ70106.1 | G | ACJ70110.1 |

All of the amino acid sequences (and nucleotide sequences where applicable) associated with these accession numbers are incorporated herein by reference as they exist in the database as of the date of the filing of this application or patent.

While as described briefly above certain illustrative embodiments of this disclosure are demonstrated using recombinant proteins comprising luciferase and C-terminal segments of N proteins from Nipah virus N protein and parainfluenza virus 5 (PIV5) NP protein, it is considered that C-terminal portions of nucleocapsid protein (as well as any other VLP components) from any paramyxovirus can be used, and can be fused to any foreign polypeptide. Evidence that this strategy applies generally to the paramyxoviruses is provided in FIG. 2 (PIV5), FIG. 5 (Nipah virus), and FIG. 10 (mumps virus). Evidence that this strategy applies generally to foreign proteins to be used as cargo is provided in FIG. 2 (*Renilla* luciferase, FIG. 4 (superoxide dismutase), and FIG. 10 (SerpinB3). Thus, the disclosure encompasses recombinant proteins comprising a distinct polypeptide and C-terminal segments from proteins of any member of the group Paramyxoviridae. In embodiments, the disclosure includes C-terminal segments of nucleocapsid (N) proteins from a member of the group Paramyxovirinae, or a member of the group Pneumovirinae. In certain examples the C-terminal segment of nucleocapsid protein is from a parainfluenza virus, including those with tropism for humans and non-human animals, the latter group comprising but not necessarily limited to avian animals, and non-human mammals, such as canines, felines, porcine and bovine mammals. In certain and non-limiting examples the C-terminal segments of nucleocapsid proteins are from a group comprising PIV5, human parainfluenza virus type 2 (hPIV2), Nipah virus (NiV), mumps virus (MuV), measles virus (MeV), Newcastle disease virus (NDV), Sendai virus (SeV), respiratory syncytial virus (RSV), and human metapneumovirus (hMPV). Any strain of such virus types are also encompassed in this disclosure. Each of these types of virus may also be a source for a wild-type or modified protein that is also a component of the VLPs of this disclosure and the amino acid sequences of such proteins are known in the art. In this regard, in one aspect the present disclosure generally relates to paramyxovirus-like particles that comprise or consist of: (1) a viral matrix protein; (2) a viral attachment glycoprotein; (3) a viral fusion glycoprotein; and (4) a foreign protein that has been modified as described herein so that it will interact with M and be incorporated into the VLPs. It will be recognized by those skilled in the art that, because the VLPs harbor the attachment and fusion glycoproteins, they are capable of binding to target cells and delivering the modified foreign protein to the cytoplasm of the target cells. It will also be recognized by those skilled in the art that, due to the natural paramyxovirus entry mechanism that involves fusion of the viral membrane directly with the target cell plasma membrane, modified foreign proteins delivered using this strategy will be transferred directly to the target cell cytoplasm and will not be delivered via the endosomal pathway (in contrast to many alternative strategies for protein delivery). It will further be recognized by those skilled in the art that many paramyxoviruses such as PIV5 and mumps virus bind to sialic acid receptors, and hence the corresponding VLPs can deliver their contents generically to nearly any kind of cell that expresses sialic acid receptors. Other paramyxoviruses such as Nipah virus and measles virus bind to protein receptors, and hence the corresponding VLPs have a specificity for target cell recognition that matches with the natural tropisms for those viruses. Furthermore, it will be recognized that technology exists to "re-target" paramyxovirus attachment proteins, making it so that the viruses only infect particular cells that express a marker protein of interest (Msaouel, P., I. D. Iankov, C. Allen, S. J. Russell, and E. Galanis. 2012. Oncolytic measles virus retargeting by ligand display. *Methods Mol Biol* 797: 141-162). Thus, paramyxovirus attachment proteins can be supplemented with or replaced by other targeting proteins, including but not necessarily limited to antibodies and antigen binding fragments thereof, receptor ligands, and other approaches that will be apparent to those skilled in the art given the benefit of the present disclosure. Hence, the range of cells that can be targeted for VLP-mediated delivery can be broad or narrow, depending on the nature of the viral attachment protein that is used for VLP production. The invention thus specifically relates to modifications that can be made to foreign proteins that will impart to them the capability to be incorporated into paramyxovirus VLPs irrespective of the nature or properties of the attachment protein(s), and to the VLPs themselves that comprise the foreign proteins.

In a demonstration of one non-limiting embodiment of the present disclosure, we produced such VLPs by introducing four distinct DNA plasmids simultaneously into cells. Such cells successfully produce the VLPs, and thus may be referred to as producer cells. In certain aspects the disclosure thus includes cells comprising one, two, three or four distinct polynucleotides (including but not necessarily limited to distinct polynucleotides that may be maintained as episomal elements), wherein the polynucleotides encode a paramyxovirus viral matrix protein, a paramyxovirus attachment glycoprotein, a paramyxovirus fusion glycoprotein and a foreign protein that can be incorporated into the VLP. (Glycosylation may be added during or postranslationally.) In alternative embodiments, fewer than four distinct polynucleotides can be used. Thus, the four VLP components can be encoded by 4, 3, 2, or 1 polynucleotide. In certain aspects, cells can be engineered to stably express any one or more of the VLP components. Such stable expression can be achieved using a variety of approaches known to those skilled in the art given the benefit of the present disclosure, and include but are not limited to chromosomally integrated polynucleotides, or by using selection agents to maintain one or more episomal elements that encode one or more of the four VLP components. Cell lines encoding 1, 2, 3 or 4 of the of the VLP components are therefore included in the scope of this disclosure, as are methods of making and using such cells and cell lines to produce VLPs. Those skilled in the art will recognize that the viral "fusion glycoprotein" is a particular type of viral protein incorporated into VLPs, and is therefore distinct from a recombinant (fusion) protein that comprises a foreign protein and a C-terminal portion of a viral N protein.

In certain embodiments, the C-terminal portion of the N protein that is a component of the modified foreign protein is from 10-120 amino acids in length, inclusive, and including all integers and ranges of integers there between. Thus, in certain embodiments, the entire C-terminal domain of a paramyxovirus nucleocapsid protein can be a component of the recombinant protein. In specific examples, the C-terminal portion of the N protein is at least 10 amino acids in length. Specific examples include amino acid lengths from 10-11, 10-12, 10-13, 10-14, 10-15, 10-16, 10-17, 10-18, 10-19, 10-20, 10-21, 10-22, 10-23, 10-24, 10-25, 10-26, 10-27, 10-28, 10-29, 10-30, 10-31, 10-32, 10-33, 10-34, 10-35, 10-36, 10-37, 10-38, 10-39, 10-40, 10-41, 10-42, 10-43, 10-44, 10-45, 10-46, 10-47, 10-48, 10-49, 10-50, 10-51, 10-52, 10-53, 10-54, 10-55, 10-56, 10-57, 10-58, 10-59, 10-60, 10-61, 10-62, 10-63, 10-64, 10-65, 10-66, 10-67, 10-68, 10-69, 10-70, 10-71, 10-72, 10-73, 10-74, 10-75, 10-76, 10-77, 10-78, 10-79, 10-80, 10-81, 10-82, 10-83, 10-84, 10-85, 10-86, 10-87, 10-88, 10-89, 10-90, 10-91, 10-92, 10-93, 10-94, 10-95, 10-96, 10-97, 10-98, 10-99, 10-100, 10-101, 10-102, 10-103, 10-104, 10-105, 10-106, 10-107, 10-108, 10-109, 10-110, 10-111, 10-112, 10-113, 10-114, 10-115, 10-116, 10-117, 10-118, 10-119, and 10-120 amino acids. In specific examples, the C-terminal portion of the N protein consists of 10, 15, or 30 amino acids. In non-limiting embodiments, the C-terminal portion of the N protein can comprise or consist of any of the N sequences for which a sequence identifier is provided in this disclosure.

The amino acid sequences of N proteins from a variety of paramyxoviruses are known in the art as discussed above, and it is contemplated that the C-terminal segments of any such paramyxoviruses can be used and/or modified for use with embodiments of this disclosure. In non-limiting examples the C-terminal portion of the N protein comprises 10 C-terminal residues from Nipah virus N protein, or 15 C-terminal residues from PIV5 NP protein. In non-limiting examples the C-terminal portion is selected from amino acid sequences that comprise or consist of the following sequences. Without intending to be bound by any particular theory it is considered that the bold amino acids are important for use in embodiments of this disclosure:

SEQ ID NO: 1
. . . QNAAVGAPIHTDDLNAALGDLDI PIV5

SEQ ID NO: 2
. . . EHGNTFPNNPNQNAQSQVGDWDE MuV

SEQ ID NO: 3
. . . DDDANDATDGNDISLELVGDFDS hPIV2

SEQ ID NO: 4
. . . SEKKNNQDLKPAQNDLDFVRADV NiV

SEQ ID NO: 5
. . . GTPQSGPPPTPGPSQDNDTDWGY NDV

SEQ ID NO: 6
. . . GRNNGVDHDEDDDTAAVAGVGGI SeV

SEQ ID NO: 7
. . . GILEEQGSDTDTPRVYNDRDLLD MeV

SEQ ID NO: 8
. . . DLTAEELEAIKHQLNPKDNDVEL HRSV

In certain examples the disclosure comprises a modified C-terminal segment of a paramyxovirus N protein wherein the modified N protein comprises at least one amino acid change relative to the unmodified (wild type) counterpart. For example, we have demonstrated that modifying a representative but non-limiting PIV5 NP protein wild type C-terminal sequence (IHTDDLNAALGDLDI (SEQ ID NO:9) to a modified sequence (IHTDDLNAALGDWDI (SEQ ID NO:10) enhances the capability of the modified sequence to direct foreign proteins into VLPs.

In certain examples more than one amino acid change can be included. Such changes can comprise conservative or non-conservative amino acid substitutions, insertions, and deletions, provided the modified C-terminal sequence retains or improves on the capability to incorporate the modified foreign protein into functional virus-like particles. In certain embodiments, an amino acid modification is introduced into a paramyxovirus N protein-derived sequence such that the sequence now directs foreign proteins to incorporate into the VLPs of a distinct paramyxovirus.

In certain aspects, "functional" virus-like particles means virus-like particles that can attach to a target cell and fuse with the target cell plasma membrane, thereby delivering the particle contents to the cytoplasm of the target cell in a way that is similar to the delivery of paramyxovirus NP-encapsidated genomes to target cells during paramyxovirus infections. As such, functional virus-like particles of this disclosure are membrane-enveloped, and are formed by budding from host "producer" cells as also described above. Because functional viral particles of this disclosure are derived from paramyxovirus components, the particles do not contain an icosahedral capsid shell, such as a capsid shell that forms the structure of papillomaviruses and other non-enveloped viruses. Such non-enveloped viruses and their corresponding VLPs are expressly excluded from the scope of this disclosure.

The disclosure includes C-terminal paramyxovirus N protein/foreign protein fusions that can be configured in distinct orientations. In certain approaches which are demonstrated in the Examples below, the fusion protein comprises in an N→C direction the foreign protein, followed by the C-terminal paramyxovirus N protein segment. Thus, the fusion protein can have at its C-terminus the paramyxovirus N protein segment. In embodiments the foreign protein and the C-terminal paramyxovirus N protein segment are contiguous. In embodiments, more than one N protein segment can be included, i.e., a foreign protein is present in a fusion protein with more than one N protein segment. The foreign protein and the C-terminal paramyxovirus N protein segment(s) may be interrupted by one or more amino acids, such as a linker, provided the linker does not negate the capability of the fusion protein to be incorporated into a functional virus-like particle. There is no particular limit to the number of linkers or the length of the linkers that can be used. In embodiments, the linker can comprise from 1-20 amino acids, inclusive, and including all integers and ranges of integers there between. In one example, a double glycine (-GG-) linker is used. In an embodiment, a sequence comprising three consecutive glycines and a serine is used, and may be repeated, and such repeated sequences may be in tandem, such as for three or more times within the fusion protein. In an embodiment, a 15 amino acid linker is used. The disclosure also comprises configurations wherein the C-terminal paramyxovirus N protein segment is positioned at the N terminus of the foreign protein, and further includes a foreign protein that is interrupted between its N and C termini with the C-terminal paramyxovirus N protein segment.

The disclosure includes polynucleotides encoding the modified paramyxovirus particles of this disclosure. The polynucleotides can be DNA, or mRNA encoding the particles, or paramyxovirus viral genome RNA. DNA or RNA can be introduced directly into cells. In certain approaches expression vectors, such as plasmids, are used. In general the expression vectors encode at least one fusion protein comprising a C-terminal paramyxovirus N protein component and the foreign protein. In certain embodiments a polynucleotide encoding foreign protein, modified with N protein-derived sequence as described in this disclosure, is integrated into a chromosome of a cell. In other embodiments the polynucleotide encoding at least one fusion protein comprising a C-terminal paramyxovirus N protein component and the foreign protein are transiently introduced into a cell, and as such can be maintained for a period of time episomally. A variety of suitable expression vectors known in the art can be adapted to produce the modified paramyxovirus particles of this disclosure. In general, the expression vector comprises sequences that are operatively linked with the sequences encoding the fusion proteins. A particular polynucleotide sequences is operatively-linked when it is placed in a functional relationship with another polynucleotide sequence. For instance, a promoter is operatively-linked to a coding sequence if the promoter affects transcription or expression of the coding sequence. Generally, operatively-linked means that the linked sequences are contiguous and, where necessary to join two protein coding regions, both contiguous and in reading frame. However, it is well known that certain genetic elements, such as enhancers, may be operatively-linked even at a distance, i.e., even if not contiguous, and may even be provided in trans. Promoters present in expression vectors that are used in the present disclosure may be endogenous or heterologous to the host cells, and may be constitutive or inducible. Expression vectors can also include other elements that are known to those skilled in the art for propagation, such as transcription and translational initiation regulatory sequences operatively-linked to the polypeptide encoding segment. Suitable expression vectors may include, for example, an origin of replication or autonomously replicating sequence (ARS) and expression control sequences, an enhancer and other regulatory and/or functional elements, such as ribosome-binding sites, RNA splice sites, polyadenylation sites, transcriptional terminator sequences, and mRNA stabilizing sequences, as well as a wide variety of selectable markers.

The expression vectors can be introduced into the host producer cells by any method known in the art. These methods vary depending upon the type of cellular host, and include but are not limited to transfection employing cationic liposomes, electroporation, calcium chloride, rubidium chloride, calcium phosphate, DEAE-dextran, or other substances as will be apparent to the skilled artisan. In certain embodiments the producer cells are mammalian cells, avian cells, or insect cells.

In one aspect the disclosure includes a kit comprising an expression vector that encodes a C-terminal segment of a paramyxovirus N protein as described above, wherein the N-protein coding sequence is configured proximal to a cloning site, such as a poly-cloning site, such that a coding region for a foreign protein can be cloned into the cloning site to be expressed in the same open reading frame as the C-terminal segment of a paramyxovirus N protein. The kit can further comprise one or more containers, printed material providing instructions as to how to use the expression vector to produce fusion proteins and/or VLPs, and reagents for introducing the expression vector into cells. Cells and cell lines comprising that express modified paramyxovirus particles as described herein are also included in this disclosure. In embodiments, the kits can comprise an N-specific viral antibody, which is useful for detecting the fusion protein.

Methods of making the modified paramyxovirus virus-like particles are included and generally comprise introducing a polynucleotide encoding a modified foreign protein together with paramyxovirus M, attachment, and fusion proteins as described herein into cells, allowing expression of the polynucleotides such that functional VLPs are formed, harvesting the VLPs from the cell culture supernatants, and (optionally) separating the functional VLPs from other components within the cell culture supernatants. Cells and cell cultures that harbor polynucleotides encoding the modified paramyxovirus VLP components are included, as are isolated and/or purified modified paramyxovirus VLP preparations. The particles, i.e., modified paramyxovirus VLPs, can be purified to any desired degree of purity using standard approaches, such as density gradient separation or commercially available kits used to purify enveloped viruses or exosomes.

In certain aspects the disclosure includes a pharmaceutical formulation comprising modified paramyxovirus VLPs as described herein. The form of pharmaceutical preparation is not particularly limited, but generally comprises modified VLPs and at least one inactive ingredient. In certain embodiments suitable pharmaceutical compositions can be prepared by mixing any one type of VLP, or combination of distinct VLPs, with a pharmaceutically-acceptable carrier, diluent or excipient, or immune response regulator, and suitable such components are well known in the art. Some examples of such carriers, diluents and excipients can be found in: Remington: The Science and Practice of Pharmacy (2005) 21st Edition, Philadelphia, Pa. Lippincott Williams & Wilkins.

In another aspect the disclosure comprises delivering to cells a foreign protein that has been modified to contain sequence derived from the C-terminal region of a paramyxovirus N protein. The method generally comprises adding a preparation of modified VLPs of this disclosure to one or more cells, such that the VLPs will attach to the cells and fuse with the target cell plasma membranes, causing the contents of the VLPs to be transferred to the cell cytoplasm.

Contacting cells with a modified VLP can be done using conventional approaches that are routinely used for infection of cells with paramyxoviruses and other enveloped viruses. The disclosure includes using the VLP to deliver the fusion protein in vitro, in vivo, and ex vivo. In embodiments the VLPs are introduced into a subject as a component of a pharmaceutical composition. In certain aspects, the VLPs can be administered using any suitable route and method which may in part be dictated by the type of foreign protein that is included in the VLP, and the subject to which the VLPs are administered. In embodiments, the amount of VLPs includes an effective amount of the foreign protein to achieve a desired result. The desired result can comprise a prophylactic effect, a therapeutic effect, or an effect that alters a trait of the recipient cells in an intended way. In this regard, the type of foreign protein that is modified with C-terminal paramyxovirus N protein segment is not particularly limited. In embodiments, the foreign protein can comprise or consist of a functional protein or fragment thereof. In certain embodiments the foreign protein is selected from enzymes, receptor ligands, transcriptional factors, growth factors, antibodies or antigen-binding fragments thereof including single-chain antibody fragments and Fabs, peptide or protein immunogens that can be used for stimulating an immune response (i.e., a vaccine), protein-based chemotherapeutic agents, and toxins. In certain embodiments, the foreign protein comprises insulin, a growth hormone or a growth hormone releasing factor, a platelet derived growth factor, an epidermal growth factor, any insulin-like growth factor, a clotting factor, superoxide dismutase and other anti-oxidant enzymes, any interferon, any interleukin, a lymphotoxin, and the like. In embodiments the foreign protein comprises a protein-based toxin, such as enzymatically active toxins which include but are not limited to diphtheria A chain, nonbinding active fragments of diphtheria toxin, exotoxin A chain (from *Pseudomonas aeruginosa*), ricin A chain, abrin A chain, modeccin A chain, alpha sarcin, *Aleurites fordii* proteins, dianthin proteins, and *Phytolaca americana* proteins (PAPI, PAPII, and PAP-S). It is expected that the length of the foreign protein will not be particularly limited. In a non-limiting embodiment, the protein is not larger in mass than the N-encapsidated viral genome that is part of a wild type paramyxovirus virion. In embodiments, the fusion protein is modified to include, for example, an intracellular trafficking signal, including but not necessarily limited to a nuclear transport signal. In certain implementations, such as when using a nuclear transport signal, the disclosure encompasses using a nuclear import inhibiting drug, suitable examples of which are known in the art and include, for instance, importazole, wherein the drug is used in producer cells during VLP production. This approach is expected to prevent the nuclear localization signal-bearing foreign protein from trafficking to the nucleus, where it may be subsequently unavailable to package into VLPs at the plasma membrane. But when the VLPs are delivered to cells in the absence of the nuclear localization inhibitor, the nuclear localization-bearing foreign protein would be able to travel to the nucleus and exert its function.

As discussed above, in one aspect the foreign protein comprises an enzyme. In non-limiting embodiments the enzyme can comprise a nuclease or a nickase (and thus may include a nuclear localization signal). In embodiments the nuclease comprises a bacterial CRISPR (clustered regularly interspaced short palindromic repeats) nuclease, including but not necessarily limited to a CRISPR Cas enzyme. In an embodiment, the Cas9 enzyme has the amino acid sequence of a Cas9 encoded by *Streptococcus pyogenes*, which are well known in the art. In embodiments, CRISPR enzyme is CRISPR enzyme that is distinct from *S. pyogenes* Cas9, which are also well known in the art. In embodiments, the Cas enzyme is a *Staph. aureus* Cas9. Alternatively, the enzyme is a Cpfl enzyme. In another embodiment, transcription activator-like effector nucleases (TALENs) can be included in the recombinant proteins. As known in the art, TALENs are artificial restriction enzymes generated by fusing a TAL effector DNA binding domain to a DNA cleavage domain and can be adapted for use in embodiments of this disclosure. In yet another approach, zinc-finger nucleases (ZFNs) can be used. Thus, in embodiments, the disclosure comprises introducing an enzyme into a cell, wherein the enzyme has nuclease and/or nickase activity, and is the foreign component of a recombinant peptide that also comprises the segment of a paramyxovirus N protein as described herein. Any cell type that is susceptible to infection by a paramyxovirus described herein can be modified by having any such enzyme introduced to it via the VLPs of this disclosure, and accordingly genetic material in the cell can be edited. The editing can comprise blunt end or sticky end cleavage. The editing can involve by homologous or non-homologous end-joining (NHEJ). The editing can involve insertions, deletions or other mutations, and can be used to make homozygous or heterozygous mutations, and thus is suitable for a wide variety of purposes, including but not limited to making knock-out and knock-in mutations.

In embodiments, the cells into which the modified VLPs, (regardless of the nature of their cargo), can comprise animal cells, including mammalian cells. In embodiments the cells are totipotent, pluripotent, multipotent, or oligopotent stem cells. In embodiments, the cells are hematopoietic stem cells. In embodiments, the cells are leukocytes. In embodiments, the leukocytes are of a myeloid or lymphoid lineage. In embodiments, the cells are embryonic stem cells, or adult stem cells. In embodiments, the cells are epidermal stem cells or epithelial stem cells. In embodiments, the cells are differentiated cells when the VLPs are introduced. In embodiments, the cells are human, or are non-human animal cells. In embodiments, the cells are used to generate cell lines, and/or transgenic non-human animals.

In embodiments, the disclosure includes obtaining cells from an individual, modifying the cells ex vivo or in vivo using any suitable CRISPR system that operates with the nuclease that is part of a recombinant protein described herein. Progeny of such cells are included. Such cells may be reintroducing to the individuals for prophylaxis and/or therapy of a condition, disease or disorder, or to treat an injury. The disclosure comprises administering nucleases suitable for CRISPR-based gene editing, and may further comprise introducing any other agents that are involved in CRISPR-based DNA editing, such as any suitable guide RNA and/or tracrRNA. In certain embodiments, the guide RNA is provided to and/or is expressed by producer cells along with the other components, for example via a plasmid. The Cas9-guide RNA complex will then be packaged into the VLPs. Kits comprising all or some of such reagents and VLPs of this disclosure are included.

In certain aspects the disclosure comprises detecting a recombinant protein and/or a cell comprising a recombinant protein of this disclosure by detecting binding of an antibody or other suitable binding partner, wherein the antibody or the other suitable binding partners binds with specificity to the paramyxovirus N protein segment of the recombinant protein. Thus immunological detection of any of the fusion proteins, and or VLPs of this disclosure is encompassed by this disclosure, as are complexes comprising antibodies or other suitable binding partners and the paramyxovirus N protein segment of the recombinant proteins. In embodiments, the binding partner comprises an antigen binding fragment of an antibody. In embodiments, monoclonal or polyclonal antibodies can be used. In embodiments, the binding partner can be detectably labeled, or can be otherwise detected using a variety of techniques known to those skilled in the art.

It will be recognized that the disclosure encompasses fusion proteins wherein the foreign protein is intended to be introduced into a cell or cell population. Individual cells and cell populations that are complexed with the VLPs, and/or into which a fusion protein of this disclosure has been introduced, are included in the disclosure.

The disclosure in certain implementations can exclude fusions of a C-terminus of a paramyxovirus N protein segment solely with polypeptide sequences that are used for purposes such as protein separation or for visualization of the fusion protein. Accordingly in certain embodiments the fusion proteins of this disclosure do not comprise a C-terminus of a paramyxovirus N protein fused solely with an affinity tag for use in protein purification, examples of which include but are not necessarily limited to chitin binding protein (CBP), maltose binding protein (MBP), glutathione-S-transferase (GST) and a poly(His) tag. Likewise, in certain embodiments, the disclosure can exclude fusions of a C-terminus of a paramyxovirus N protein with proteins that are used alone as detectable labels, including but not limited to green fluorescent protein. In other embodiments, the disclosure excludes fusion solely with polyanionic amino acids, such as found in a FLAG-tag, and can exclude fusion solely with epitope tags, which are short peptide sequences for producing high-affinity antibodies, examples of which include but are not limited V5-tag, Myc-tag, and HA-tag. Thus, embodiments of this disclosure comprise VLPs wherein the foreign protein component of the fusion does not consist only of one of the foregoing polypeptides. In particular, the foreign proteins are present in the fusion protein and are distinct from polypeptide sequences that are used for protein separation, or for visualization of the fusion protein, or as intracellular trafficking signals. However, it should be recognized that polypeptide sequences that are used for protein separation, or for visualization of the fusion protein, or as intracellular trafficking signals, or for any other purpose, may be present so long as the foreign protein is also present in the fusion protein.

In certain aspects the disclosure comprises screening for compounds that can impair viral cell entry, i.e., antiviral drugs. In this approach test agents are screened against VLPs which are modified according to embodiments of this disclosure such that they include a detectable label or reporter protein, non-limiting examples of which include fluorescent proteins, such as any green fluorescent protein (GFP), and non-fluorescent proteins such as luciferase. In certain embodiments the proteins produce a visually or machine detectable signal. In certain approaches the disclosure provides a method for screening a plurality of test agents to determine if they are candidates for use in reducing any particular virus in an individual, and/or for impairing viral cell entry. In one embodiment, the method comprises screening a plurality of test agents to identify candidates for use in reducing VLP entry into cells by: a) contacting a plurality of cells/cell samples with distinct test agents; b) adding VLPs to the plurality of cells; and subsequently c) determining VLP entry into the cells, wherein a reduction VLP entry relative to a control indicates the test agent is a candidate for use in inhibiting VLP entry into cells. Thus, antiviral agents for use in human and non-human animal (e.g., veterinary approaches) can be identified. In embodiments, the VLPs and test agents may be contacted with the cells concurrently. The plurality of cell samples is configured so as to be amenable for high throughput screening (HTS). In certain embodiments, the samples are divided into a plurality of reaction chambers, such as wells in a plate. Any multi-well plate or other container can be used. In certain approaches, one or more 384-wells plates are used, and detection of signals can be automated, and/or performed for example, by microscopy or other visual detection of a signal. Suitable controls will be evident to those skilled in the art.

Administration of formulations comprising the modified VLPs as described herein can be performed using any suitable route of administration, including but not limited to parenteral, intraperitoneal, intrapulmonary, oral, and intratumoral. Parenteral infusions include intramuscular, intravenous, intraarterial, intraperitoneal, and subcutaneous administration. The compositions can be administered to humans, and are also suitable for use in a veterinary context and accordingly can be given to non-human animals, including non-human mammals.

In embodiments and as discussed above, the modified VLPs are used to treat cells that have been separated from an individual, are contacted with the VLPs such that a particular effect on the cell is achieved by introducing the VLP into the cells, after which the cells are reintroduced to the individual, and/or are maintained as a cell line.

The following Examples are intended to illustrate but not limit embodiments of this disclosure.

Example 1

This Example provides a description of the materials and methods used to generate paramyxovirus VLPs, to incorporate foreign proteins into paramyxovirus VLPs, and to measure the incorporation efficiency.

Plasmids. The plasmids pCAGGS-PIV5 M, pCAGGS-PIV5 NP, and pCAGGS-PIV5 HN have been described before (Schmitt A P, Leser G P, Waning D L, Lamb R A. 2002. Requirements for budding of paramyxovirus simian virus 5 virus-like particles. J. Virol. 76:3952-3964), as have plasmids pCAGGS-MuV M, pCAGGS-MuV NP, pCAGGS-MuV F, pCAGGS-NiV M, and pCAGGS-NiV N (Li M, Schmitt P T, Li Z, McCrory T S, He B, Schmitt A P. 2009. Mumps virus matrix, fusion, and nucleocapsid proteins cooperate for efficient production of virus-like particles. J. Virol. 83:7261-7272). Site-directed mutants of PIV5 and mumps virus NP genes were generated by PCR mutagenesis of the wt sequences and the resulting cDNAs were subcloned into the eukaryotic expression vector pCAGGS (33). cDNA corresponding to *Renilla* luciferase was obtained by PCR amplification of its coding sequence from plasmid pSMG-RLuc. This sequence was modified using PCR to incorporate C-terminal sequences derived from PIV5 NP or Nipah virus N, with an additional double glycine (-GG-) linker added between the luciferase and virus-derived sequences. The resulting cDNAs were subcloned into the pCAGGS vector. pCAGGS-RLuc-N15 was further modified by PCR mutagenesis to generate a set of alanine substitution mutants. DNA sequencing of the entire genes was carried out to verify their identities (Genomics Core Facility, Pennsylvania State University). cDNAs corresponding to human superoxide dismutase (SOD1) and human SerpinB3 were likewise modified using PCR to incorporate C-terminal sequences derived from PIV5 NP or Nipah virus N, with the double glycine linker added between the human- and virus-derived sequences. These sequences were further modified by PCR to incorporate N-terminal Myc tags (amino acid sequence N-EQKLISEEDL-C(SEQ ID NO:11).

Antibodies. PIV5 M and NP proteins were detected using the monoclonal antibodies M-f and NP-a. PIV5 HN protein was detected using the polyclonal antibody SDS-HN. Mumps virus M, NP, and F proteins were detected using polyclonal anti-peptide antibodies that are known in the art. Nipah virus M and N proteins were detected using polyclonal antibodies raised against the corresponding full-length recombinant proteins. *Renilla* luciferase was detected using a polyclonal antibody purchased from MBL International (Woburn, Mass.).

Membrane co-flotation assays to measure M-NP protein interactions. 293T cells in 6-cm-diameter dishes, grown in Dulbecco's modified Eagle medium (DMEM) supplemented with 10% fetal bovine serum, were transfected with pCAGGS plasmids encoding M and/or NP proteins (1.2 μg and 800 ng of plasmid DNA, respectively). Lipofectamine-Plus reagents in Opti-MEM were used for transfection (Invitrogen, Carlsbad, Calif.). Cells were harvested at 24 h post transfection (p.t.), and re-suspended in a hypotonic solution (25 mM NaCl, 50 mM $Na_2HPO_4$, pH 7.4; 1 mM phenylmethyl-sulfonyl fluoride). The cell suspension was incubated for 20 min with rocking at 4° C. Cells were then disrupted by passaging them through a 23-gauge needle 20 times, and these cellular extracts were centrifuged at 1,500×g for 5 min at 4° C. to remove nuclei and cell debris. The resulting supernatants were mixed with 1.5 ml of 80% sucrose in NTE (0.1 M NaCl; 0.01 M Tris-HCl, pH 7.4; 0.001 M EDTA). A sucrose gradient was then formed by overlaying these samples with 50% sucrose (2.4 ml) and 10% sucrose (0.6 ml) solutions in NTE. Samples were subjected to ultracentrifugation at 160,000×g for 4 h in a Beckman SW55Ti rotor. Four fractions were collected from the top of each gradient and 2% of each fraction was loaded on 10% sodium dodecyl sulfate-polyacrylamide gel electrophoresis (SDS-PAGE) gels and resolved. Proteins were subjected to immunoblotting with antibodies specific to the viral M and/or NP proteins. Protein bands were detected and quantified using a Fuji FLA-7000 laser scanner (FujiFilm Medical Systems, Stamford, Conn.). The amount of NP protein in membrane fractions was quantified by measuring the NP protein in the top two fractions divided by the sum of the NP protein in all four fractions.

Measurements of VLP production. 293T cells in 6-cm-diameter dishes at about 70-80% confluency, grown in DMEM supplemented with 10% fetal bovine serum were transfected with pCAGGS plasmids encoding PIV5, mumps virus, or Nipah virus proteins for production of PIV5, mumps virus, or Nipah virus-like particles (VLPs). Lipofectamine-Plus reagents in Opti-MEM were used for plasmid transfection. Plasmid quantities per dish were as follows—pCAGGS-PIV5 M—400 ng, pCAGGS-MuV M—400 ng, pCAGGS-NiV M—400 ng, pCAGGS-PIV5 NP and derivatives—100 ng, pCAGGS-MuV NP and derivatives—100 ng, pCAGGS-NiV N—100 ng, pCAGGS-RLuc—100 ng, pCAGGS-RLuc-PIV5 NP/NiV N fusions—100 ng, pCAGGS-PIV5 HN—1.5 ug, pCAGGS-MuV F—100 ng. To keep total plasmid amounts equal during transfection, an empty pCAGGS plasmid that does not encode any viral protein was included as necessary.

At 24 h p.t., the culture medium was replaced with DMEM containing 2% fetal bovine serum, or for metabolic labeling experiments, with DMEM containing one-tenth the normal amount of cysteine and methionine, along with 37 μCi of ($^{35}$S) Promix/ml (Perkin Elmer, Waltham, Mass.). After an additional 16-18 h, cells and media were harvested. First, culture media were centrifuged at 8,000×g for 2 min to remove cell debris. The supernatants were then layered onto 20% sucrose cushions (4 ml in NTE). Samples were centrifuged at 140,000×g for 1.5 h, after which pellets containing VLPs were resuspended in 0.9 ml of 1× phosphate-buffered saline (PBS) (0.13 M NaCl; 2.6 mM KCl; 1.4 mM $KH_2PO_4$; 8.0 mM $Na_2HPO_4.7H_2O$; pH 7.4), and mixed with 2.4 ml of 80% sucrose in NTE. Layers of 50% sucrose in NTE (3.6 ml) and 10% sucrose in NTE (0.6 ml) were applied to the tops of the gradients, and these were then centrifuged at 140,000×g for 3 h. 4 ml was collected from the top of each gradient, and the VLPs contained in this fraction were pelleted by centrifugation at 190,000×g for 1.5 h. VLP pellets were then resuspended in SDS-PAGE loading buffer containing 2.5% (wt/vol) dithiothreitol.

To prepare cell lysates, a third of the cells from each sample were lysed with 0.1 ml of SDS-PAGE loading buffer. The lysates were centrifuged through QIAshredder homogenizers (Qiagen, Germantown, Md.) to break up cell debris. Cell lysates and purified VLPs were fractionated by SDS-PAGE using 10% gels, and proteins were detected by immunoblotting using antibodies specific to the viral proteins and/or *Renilla* luciferase. Imaging and quantification was performed using a FUJI FLA-7000 laser scanner. PIV5 and mumps VLP production was measured by calculating the amount of PIV5 M protein or mumps virus M protein in VLPs, normalized to the amount of M protein present in cell lysates. Luciferase protein incorporation into Nipah VLPs was calculated as the amount of luciferase protein in particles, divided by the amount of M protein in particles.

Amino acid sequence comparisons. To compare C-termini of paramyxovirus nucleoprotein sequences, data was derived from GenBank files with the following accession numbers, which include whole genome information from these viruses: PIV5, AF052755; mumps virus, JN012242; Nipah virus, AF212302; human parainfluenza virus type 2 (hPIV2), M55320; measles virus, AB016162; Sendai virus, M30202; Newcastle disease virus (NDV), AF064091; Hendra virus, AAC83187; human respiratory syncytial virus (HRSV), AE045904. The sequences of each of the nucleotide and amino acid sequences associated with these accession numbers are incorporated herein by reference as they are present on the filing date of this application or patent.

Example 2

This Example provides a demonstration showing manipulation of genome packaging interactions to direct the foreign protein *Renilla* luciferase into PIV5 VLPs.

Figure 3:
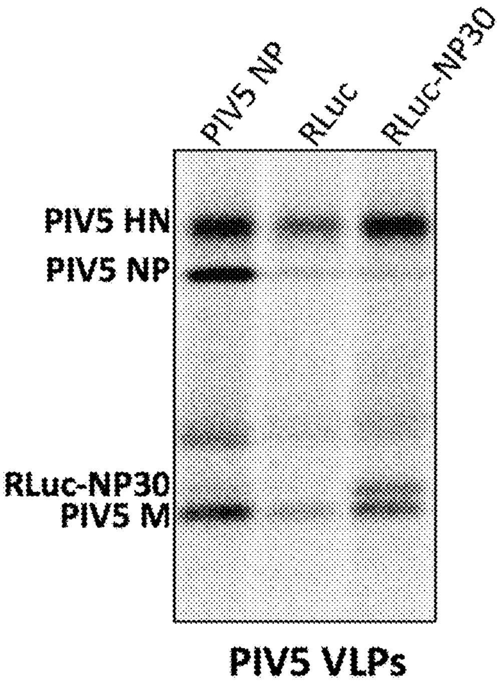
FIG. 3. Data showing efficient packaging of RLuc-NP30 into PIV5 VLPs demonstrated by metabolic labeling. 293T cells were transfected to produce PIV5 M and HN proteins together with unmodified RLuc, or RLuc-NP30. Cells were metabolically labeled, VLPs were purified by centrifugation through sucrose cushions followed by flotation on sucrose gradients, and the purified VLPs were loaded directly onto SDS gels. VLP-derived proteins were detected using a phosphorimager. The data show that RLuc-NP30 was efficiently incorporated into VLPs, such that the amount of RLuc-NP30 in the VLPs was similar to the amount of viral M protein.

We identified a DLD sequence (highlighted in FIG. 7) near the C-terminal end of PIV5 NP protein that without intending to be bound by any particular theory is considered to be important for M-binding and for efficient VLP production (Schmitt P T, Ray G, Schmitt A P. 2010. The C-terminal end of parainfluenza virus 5 NP protein is important for virus-like particle production and M-NP protein interaction. J. Virol. 84:12810-12823). We transplanted segments from the C-terminal end of PIV5 NP onto the C-terminal end of *Renilla* luciferase (RLuc), as illustrated in FIG. 2A. The luciferase proteins were expressed together with PIV5 M and HN proteins in 293T cells for VLP production. The unmodified RLuc reporter protein completely lacked VLP assembly functions, as expression of RLuc together with PIV5 M and HN proteins led to poor VLP production, similar to that observed when M and HN proteins were expressed alone (FIG. 2B). In contrast, expression of M and HN proteins together with PIV5 NP protein led to highly efficient VLP production. VLP production was quantified based on the amount of viral M protein detected in sucrose-gradient purified VLPs, normalized to the amount of M detected in cell lysate fractions (FIG. 2B). Thus, the present disclosure includes measuring efficiency of VLP production, and includes in embodiments having at least a certain amount of VLP production relative to a suitable control, such as VLP production with an unmodified N protein or unmodified foreign protein. Fusion of either 5 residues or 10 residues from NP to the C-terminal end of RLuc had little impact on VLP production. However, if 15 or more residues were appended to RLuc, the modified RLuc unexpectedly gained the ability to stimulate VLP production. RLuc-NP15 expression led to VLP production that was about 60% of that observed with the authentic viral NP protein, and RLuc-NP30 and RLuc-NP50 each led to VLP production that was roughly equivalent to that observed with the authentic NP (FIG. 2B). Moreover, substantial quantities of modified RLuc were found within the purified VLP preparations (FIG. 2B). To more directly assess the incorporation efficiency, VLPs were produced in cells that were metabolically labeled with $^{35}$S amino acids. VLPs were purified, loaded directly on SDS gels, and proteins detected using a phosphorimager for visualization of VLP polypeptide composition. The result indicated that RLuc-NP30 was abundantly packaged into VLPs, at a level that was comparable to that of viral M protein (FIG. 3). The ratio of RLuc-NP30 to M protein in the purified VLPs was 1.1:1.0, taking into account the numbers of methionine and cysteine residues present in the respective proteins.

Example 3

This Example provides a demonstration showing manipulation of genome packaging interactions to direct the foreign protein SOD1 into PIV5 VLPs.

Figure 4:
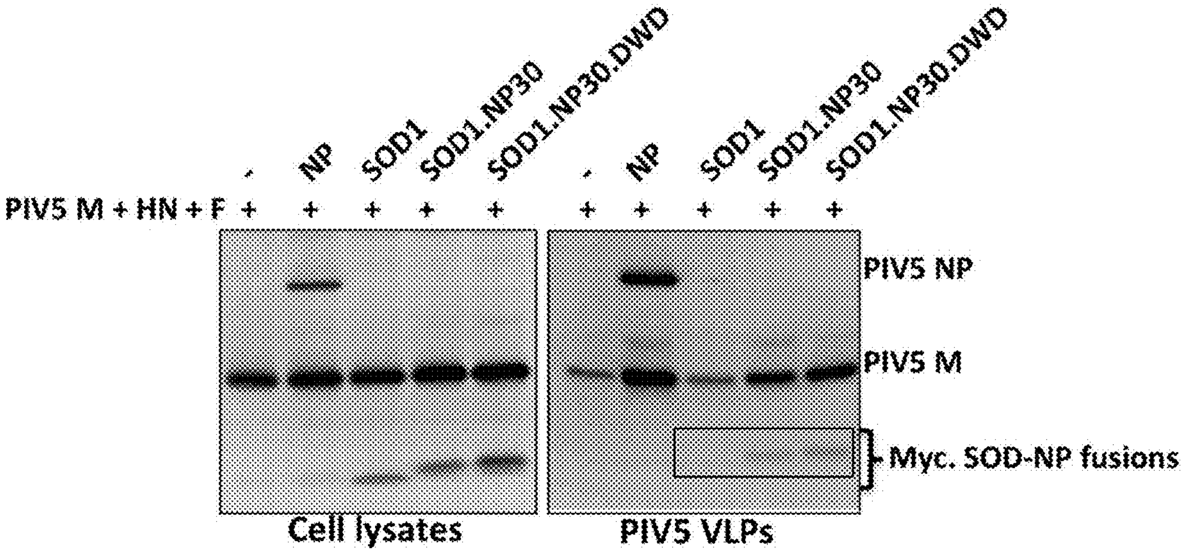
FIG. 4. Data showing manipulation of paramyxovirus genome packaging interactions to direct superoxide dismutase into PIV5 VLPs. 30 amino acid residues from the C-terminal end of PIV5 NP protein were transplanted onto the C-terminal end of superoxide dismutase (SOD1) to generate SOD1.NP30. SOD1.NP30.DWD is identical to SOD1.NP30 except that a single amino acid residue has been changed, converting the DLD sequence within the NP30 region to DWD. 293T cells were transfected to produce PIV5 M, HN, and F proteins together with the indicated SOD1-NP fusions. VLPs released into the culture supernatants were purified by centrifugation through sucrose cushions followed by flotation on sucrose gradients. Viral proteins from cell lysate and purified VLP fractions were detected by immunoblotting. SOD1.NP30 and SOD1.NP30.DWD both succeeded in triggering VLP release, and were recovered in the VLPs to a much greater extent than unmodified SOD1.

Modification of a foreign protein and incorporation of the foreign protein into PIV5 VLPs was carried out as in Example 2, but in this case superoxide dismutase (SOD1) was used as the foreign protein instead of *Renilla* luciferase (FIG. 4). The SOD1 protein was modified by appending to its C-terminal end the 30 amino acid residues derived from the C-terminal end of PIV5 NP protein. Similar to the results obtained with *Renilla* luciferase (FIG. 3B), the modified SOD1 protein stimulated VLP production and was incorporated into the VLPs (FIG. 4, VLP fraction, lane 4). SOD1 protein without the C-terminal modification was not incorporated into the VLPs (FIG. 4, lane 3). Further modification of the appended sequence, changing DLD to the DWD sequence that is found in the mumps virus NP protein, led to a moderate enhancement of SOD1 incorporation (FIG. 4, lane 5). This result indicates that the strategy used for directing foreign proteins into paramyxovirus VLPs is likely to be widely applicable, and not dependent on the nature of the foreign protein that has been selected for VLP incorporation.

Example 4

This Example provides a demonstration showing manipulation of genome packaging interactions to direct the foreign protein *Renilla* luciferase into Nipah VLPs.

Figure 5:
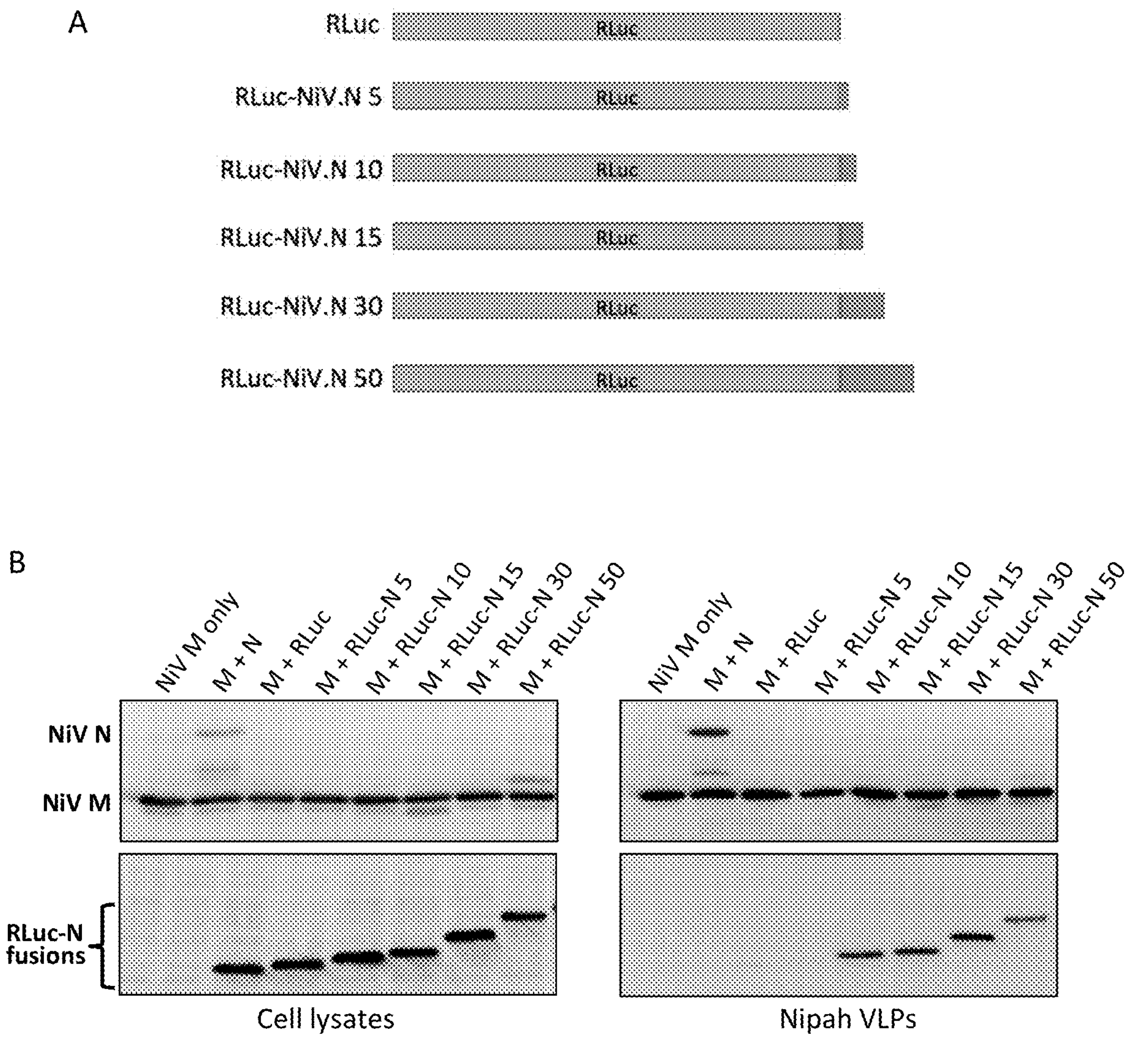
FIG. 5. Data showing manipulation of paramyxovirus genome packaging interactions to direct *Renilla* luciferase into Nipah VLPs.

Sequences within the Nipah virus N protein that function to coordinate with M protein during virus assembly have not been defined. Here, we hypothesized based on analogy with PIV5 that such sequences might be located near the C-terminal end of N protein. To test this hypothesis, we transplanted segments from the C-terminal end of Nipah virus N onto the C-terminal end of RLuc. The luciferase proteins were expressed together with Nipah virus M protein, and incorporation of RLuc into the budding VLPs was measured (FIG. 5). It is important to note that in the case of Nipah virus, VLP production does not depend on expression of N protein or glycoproteins—VLPs are produced efficiently upon expression of Nipah virus M protein alone. However, N protein is incorporated into the M-containing VLPs when it is co-expressed (FIG. 5B, lane 2). We found that unmodified RLuc was incorporated poorly into M-VLPs (FIG. 5). Fusion of 5 residues derived from N to the C-terminal end of RLuc did not improve its incorporation into VLPs. However, if 10 residues were appended to RLuc, incorporation into VLPs improved, and if 15 or 30 residues were appended to RLuc, VLP incorporation was improved still further, to a level that was approximately 2.5-times greater than that observed with the unmodified RLuc control (FIG. 5). RLuc-N50 was incorporated somewhat less efficiently into VLPs than RLuc-NP15 or RLuc-NP30, but its incorporation was still approximately 1.5-fold higher than that observed with the unmodified RLuc control. Overall, our results with Nipah virus and PIV5 demonstrate that foreign proteins can be engineered for packaging into budding paramyxovirus VLPs through addition of small (10-15 residue) appendages to their C-terminal ends.

Example 5

Figure 6:
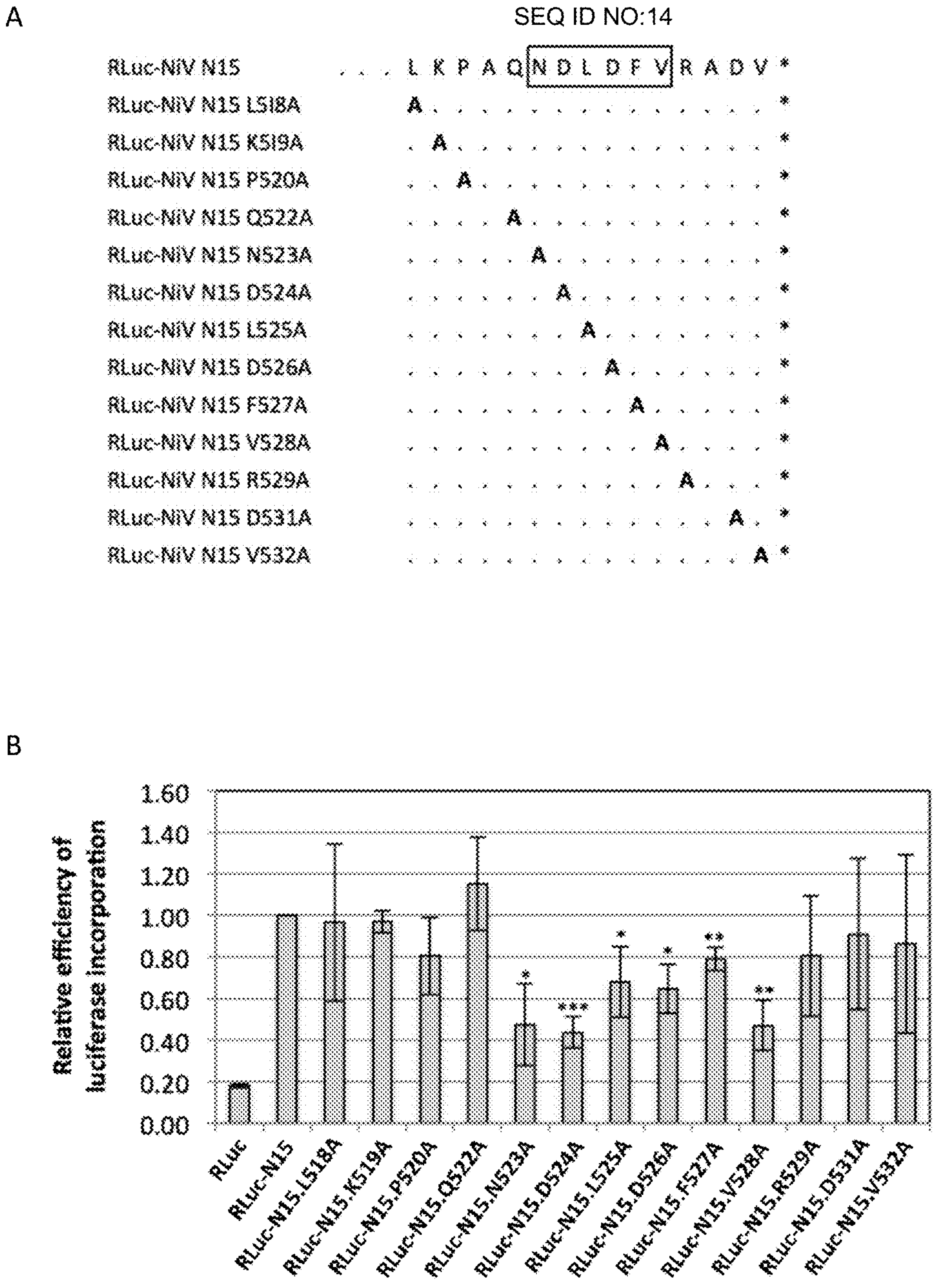
FIG. 6. Data showing amino acid residues 523-NDLDFV-528 (SEQ ID NO:12) within Nipah virus N protein are important for the ability to direct a foreign protein into Nipah VLPs.

This Example demonstrates that amino acid residues 523-528 of N protein are important for RLuc packaging into Nipah VLPs. The C-terminal 15 residues of Nipah virus N protein were targeted by alanine-scanning mutagenesis to determine which of these residues are necessary for efficient direction of the RLuc reporter into Nipah VLPs (FIG. 6A). The altered RLuc proteins were co-expressed together with Nipah virus M protein, and RLuc incorporation into VLPs was measured. Substitutions at any of the positions from residues 523-528 caused significant reduction in luciferase incorporation (FIG. 6 B,C). The most severe defects were associated with changes at positions N523 and D524. In those cases, luciferase incorporation into VLPs was similar to that observed with the unmodified luciferase control (FIG. 6 B,C). Alanine substitutions targeting the surrounding residues, outside of the sequence 523-NDLDFV-528 (SEQ ID NO:12), had little impact on luciferase incorporation into VLPs.

Example 6

Figures 6, 7:
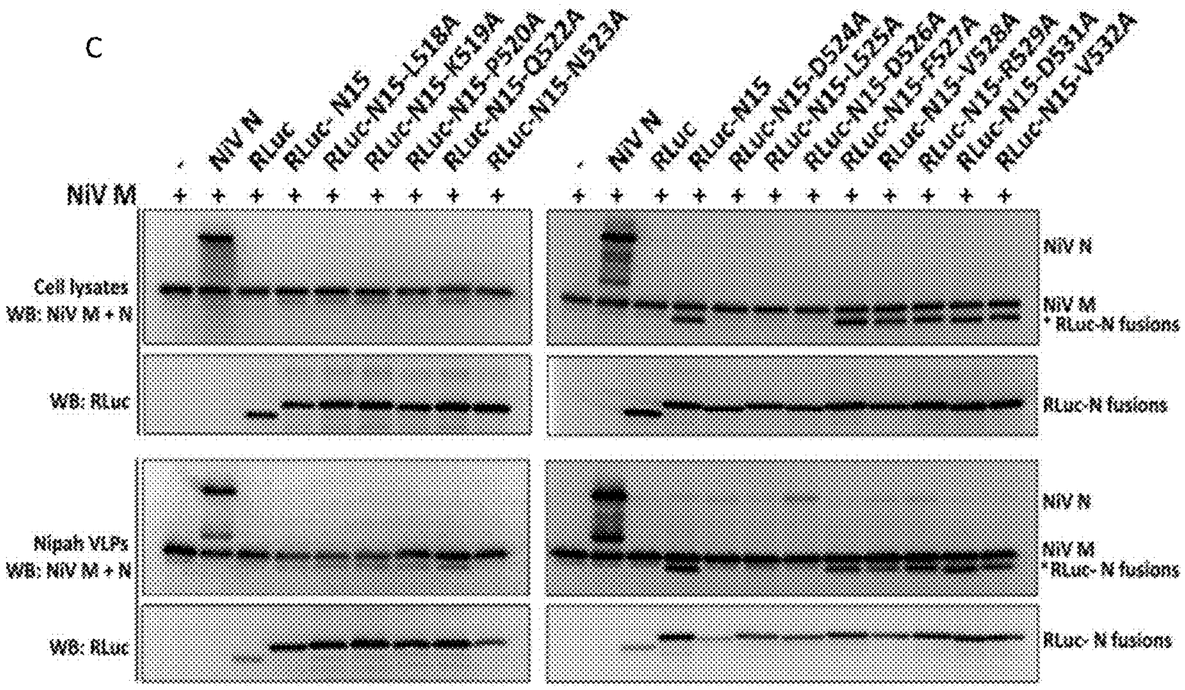
FIG. 7. Amino acid sequences of C-terminal ends of paramyxovirus N/NP proteins. The upper portion includes sequences derived from paramyxoviruses within the Rubulavirus genus, while the lower portion includes sequences derived from paramyxoviruses outside of the Rubulavirus genus. DLD-like sequences are highlighted in bold.
Figure 8:
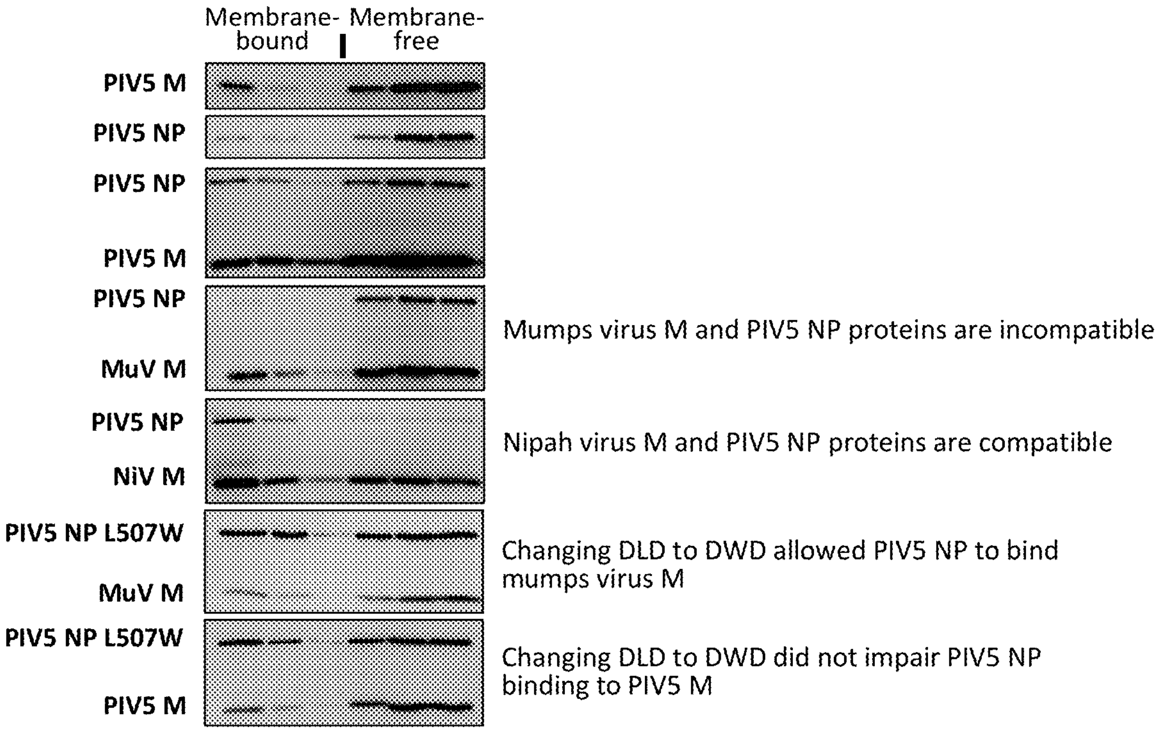
FIG. 8. Data showing that DLD and DWD sequences define binding compatibilities between PIV5 and mumps virus M/NP protein pairs. 293T cells were transfected to produce M and/or NP proteins as indicated. Detergent-free cell extracts were prepared and placed at the bottoms of sucrose flotation gradients. After centrifugation to allow flotation of membrane-bound proteins, fractions were collected from the tops of the gradients and viral proteins were visualized by immunoblotting. Mumps virus M protein was unable to recruit the DLD-containing PIV5 NP protein to the membrane-bound fraction of the gradient, but a single amino acid change converting DLD to DWD induced compatibility between these proteins, allowing recruitment of PIV5 NP L507W to the membrane-bound fraction of the gradient.

This Example demonstrates that PIV5 NP protein and mumps virus M protein can be engineered for compatibility. In contrast to the PIV5 and Nipah virus nucleocapsid proteins which harbor DLD sequences near their C-terminal ends, the NP protein of mumps virus lacks DLD near its C-terminal end (FIG. 7). This raised the possibility that PIV5 and mumps virus might be incompatible with respect to M-NP interactions, despite being very closely related viruses overall (both within the Rubulavirus genus of the paramyxoviruses). To test this, mumps virus M protein was expressed together with PIV5 NP protein, and interaction between the two proteins was measured using a membrane co-flotation assay (FIG. 8). Mumps M was found to be incompatible with PIV5 NP, judged by its failure to induce PIV5 NP protein to associate with the membrane-bound fraction together with M (FIG. 8). In contrast, PIV5 M protein is compatible with PIV5 NP, and induces NP to associate with the membrane-bound fraction. Nipah virus M protein is also compatible with PIV5 NP, judged by NP flotation in this assay (FIG. 8). Interestingly, if a single amino acid change, L507W, is introduced into PIV5 NP to convert DLD to the DWD sequence that is normally found in mumps virus NP, the protein now gains compatibility with mumps virus M judged by membrane co-flotation (FIG. 8). These results indicate that PIV5 NP protein is incompatible for interaction with mumps virus M, and that compatibility can be induced through a single amino acid change that converts the C-terminal DLD sequence to DWD.

Figure 9:
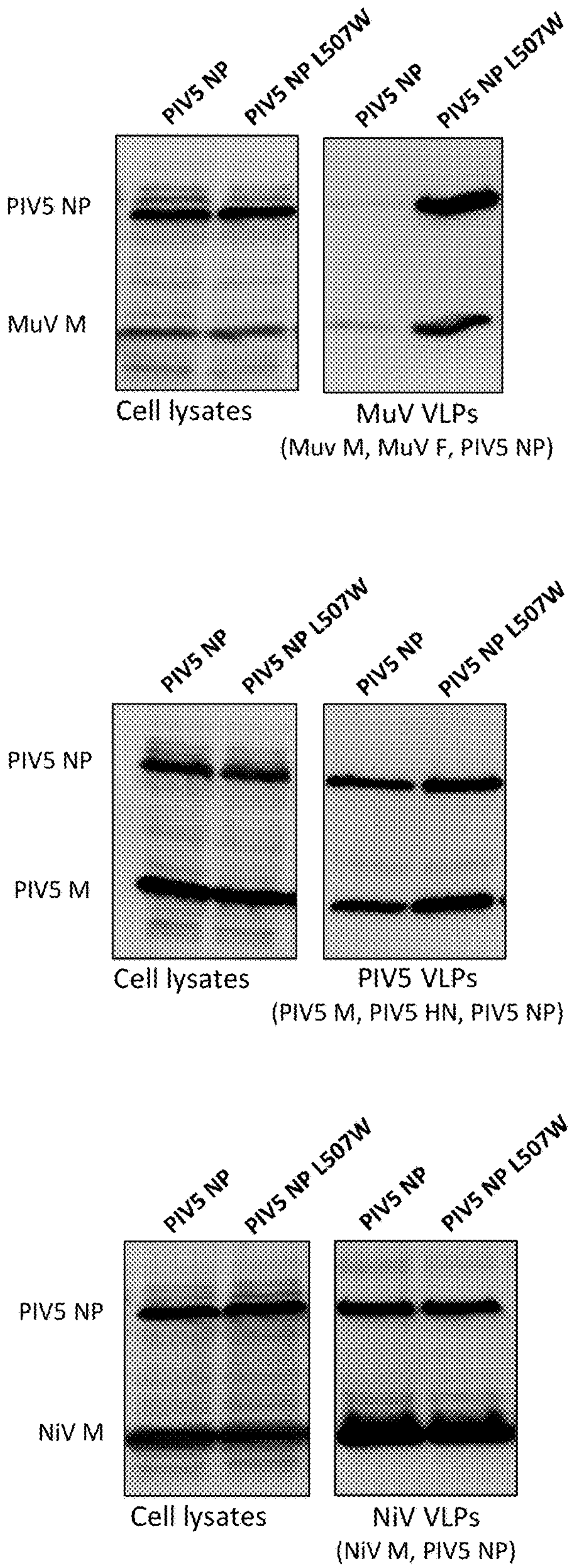
FIG. 9. Data showing DLD and DWD sequences define VLP production compatibilities between PIV5 and mumps virus M/NP protein pairs. Left panel: 293T cells were transfected to produce mumps VLPs, except one critical component, mumps virus NP protein, was omitted and replaced with either the DLD-containing PIV5 NP or the DWD-containing PIV5 NP L507W. Only the DWD-containing NP protein could function for production of mumps VLPs. Center panel: Both PIV5 NP and NP 507W function to allow production of PIV5 VLPs. Right panel: Both PIV5 NP and NP 507W incorporate into Nipah VLPs.

To test if the conversion of DLD to DWD creates functional compatibility with mumps virus M protein in addition to interaction compatibility, VLP production experiments were carried out. Mumps virus M and F proteins were expressed in 293T cells for VLP production together with either the DLD-containing PIV5 NP protein or the DWD-containing PIV5 NP L507W protein. Only the DWD-containing version was able to induce significant production of mumps VLPs (FIG. 9, left panel). In contrast, the two proteins were similar in their ability to induce production of PIV5 VLPs (FIG. 9, middle panel) or to incorporate into Nipah VLPs (FIG. 9, right panel). Hence, the DWD-containing NP protein gained compatibility with mumps virus M protein without losing any of its existing compatibilities with PIV5 and Nipah virus M proteins. These results demonstrate that PIV5 NP protein can be engineered for functional compatibility with mumps virus M through a single amino acid change converting DLD to DWD. Furthermore, it can be inferred from these results that strategies for incorporating foreign proteins into mumps VLPs should benefit from the use of DWD-containing sequence appendages, as opposed to DLD-containing sequence appendages.

Example 7

Figure 10:
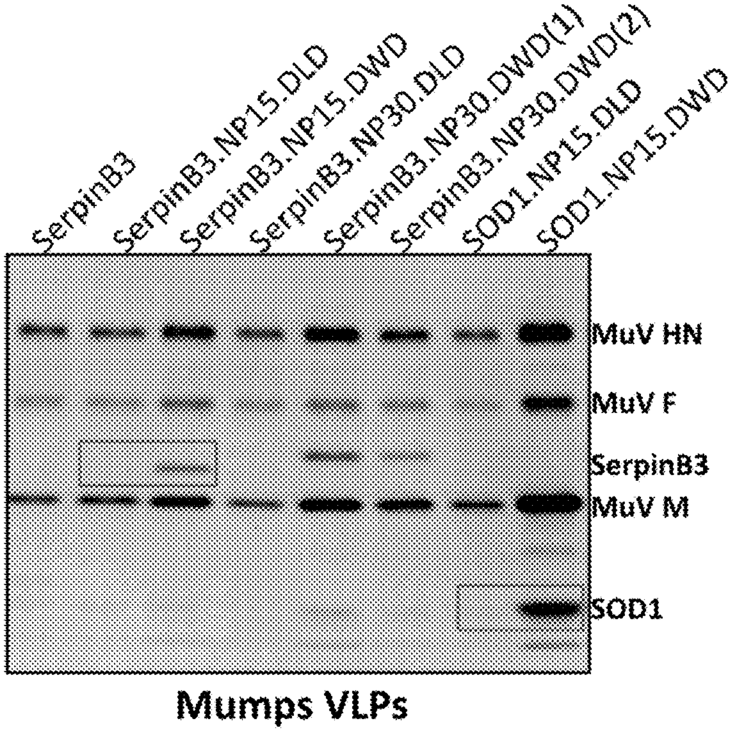
FIG. 10. Data showing mumps VLPs engineered to contain SOD1 or Serpin B3. 293T cells were transfected to produce mumps virus M, HN, and F proteins together with modified SerpinB3 protein or modified SOD1 protein as indicated. VLPs released into the culture supernatants were purified by centrifugation through sucrose cushions followed by flotation on sucrose gradients. Viral proteins from purified VLP fractions were detected by immunoblotting. SerpinB3.NP15.DWD succeeded in triggering VLP release, and was recovered in the VLPs to a much greater extent than unmodified RLuc. In this case, 15 residues from the C-terminal end of PIV5 NP has been transplanted onto the C-terminal end of SerpinB3, and the DLD sequence within NP15 has been changed to DWD. NP15.DLD sequence, in contrast, failed to induce incorporation of SerpinB3 into mumps VLPs. Similarly, SOD1 could be made to incorporate into mumps VLPs only when appended with the PIV5-derived NP15 sequence in which DLD has been changed to DWD. The NP15.DLD sequence could not induce incorporation of SOD1 into mumps VLPs.

This Example demonstrates another and non-limiting embodiment of the disclosure. In particular, we demonstrate packaging of two separate foreign proteins into mumps VLPs. Specifically, FIG. 10 provides data demonstrating successful packaging of superoxide dismutase and SerpinB3 into mumps VLPs. In each case, only DWD-containing sequence appendages, and not DLD-containing appendages, could induce the foreign proteins to package into mumps VLPs (FIG. 10, boxed regions). For example, SerpinB3 appended with PIV5 NP sequence in which DLD has been changed to DWD (SerpinB3.NP15.DWD) was effectively incorporated into mumps VLPs. In contrast, the corresponding SerpinB3 in which DLD has been left unchanged (SerpinB3.NP15.DLD) could not effectively incorporate into mumps VLPs. This Example thus provides further evidence that DWD-containing sequences facilitate incorporation of foreign proteins into modified mumps VLPs.

Example 8

Figure 11:
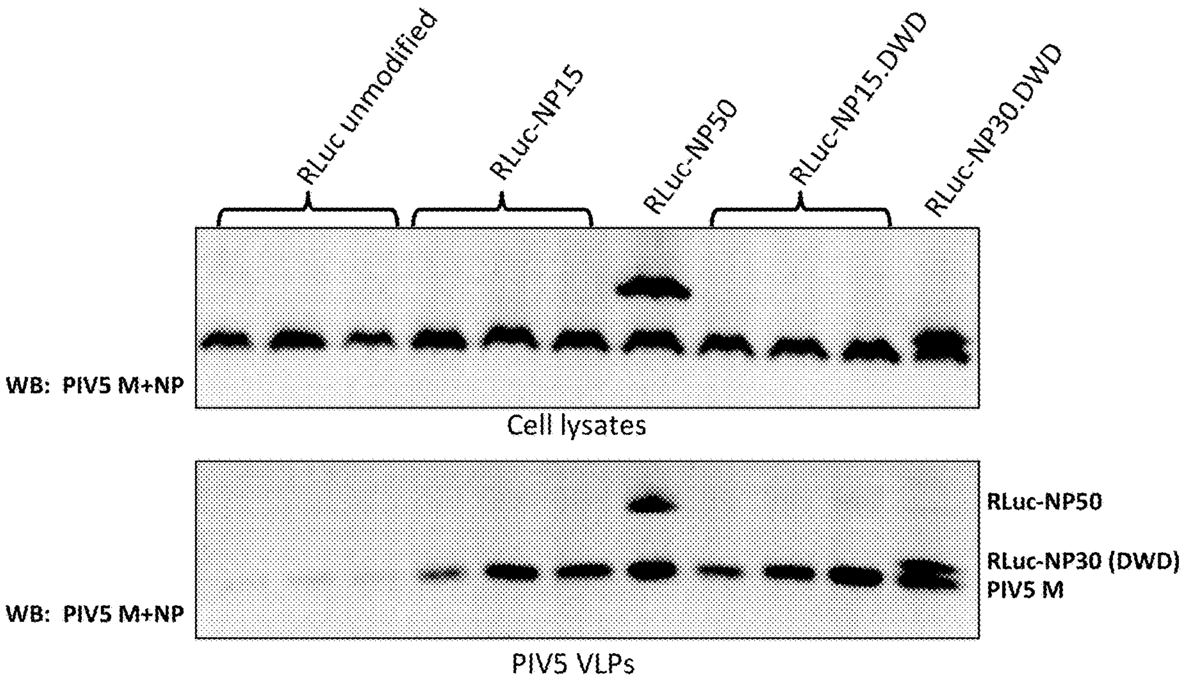
FIG. 11. Data showing C-terminal ends of paramyxovirus N/NP proteins function as epitope tags in addition to VLP incorporation sequences. 293T cells were transfected with PIV5 M and HN proteins, together with the indicated RLuc-NP fusions. VLPs released into the culture supernatants were purified by centrifugation through sucrose cushions followed by flotation on sucrose gradients. Viral proteins from purified VLP fractions were detected by immunoblotting using monoclonal antibodies specific to the viral M and NP proteins (i.e., no antibody specific to RLuc was used). RLuc-NP50 and RLuc-NP30.DWD fusion proteins were detected, indicating that the epitope recognized by NP monoclonal antibody lies within the NP30 sequence region that has been appended. DLD to DWD amino acid substitution did not prevent immunodetection.
Figure 12:
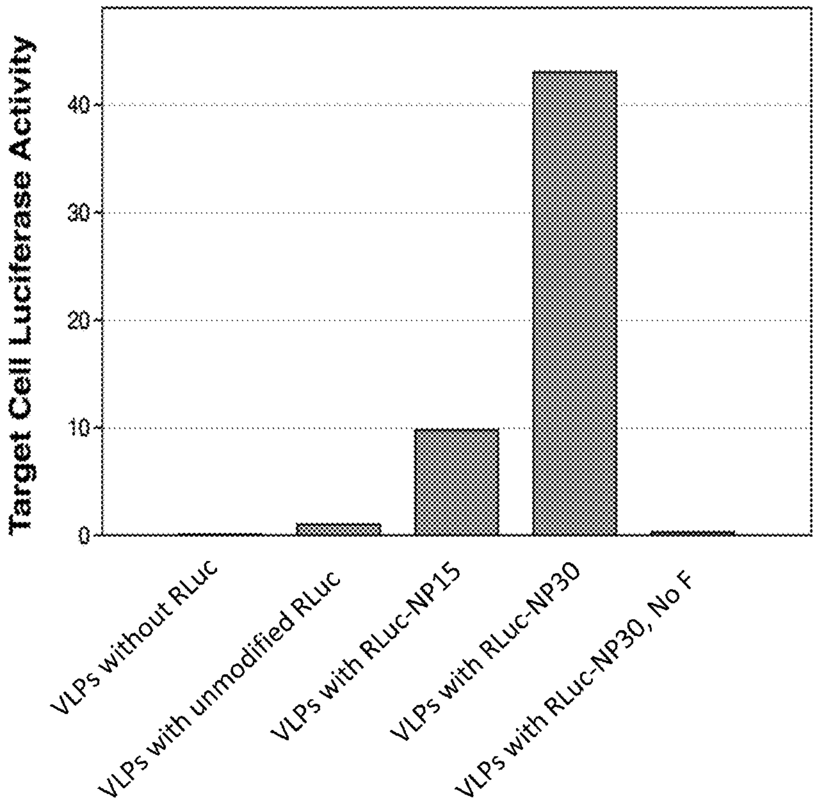
FIG. 12. Data showing delivery of a foreign protein to target cells using paramyxovirus VLPs. 293T cells were transfected to produce PIV5 M, HN, and F proteins together with RLuc-NP15 or RLuc-NP30. The resulting RLuc-loaded VLPs released into the culture supernatants were purified by centrifugation through sucrose cushions followed by flotation on sucrose gradients. The purified VLPs were incubated with Vero cells for 1 h. The Vero cells were then washed and lysed, and luciferase activity in the cell lysate was measured with a luminometer. VLPs produced with no F protein are unable to mediate fusion between the VLP membrane and the target cell membrane, and this prevented RLuc delivery to target cells.

This Example provides another demonstration of a utility of embodiments of the disclosure. In particular, this Example provided data that the C-terminal NP-derived sequences comprise epitopes that allow antibody recognition by NP-specific antibodies. Thus, for any particular protein that is desirable for intracellular delivery using aspects of this disclosure, but for which a suitable antibody is not readily available, simply adding the NP-derived sequence creates a fusion protein that can be immunologically detected by existing anti-NP antibodies. Such antibodies are available and can be used given the benefit of this disclosure to detect either the DLD or DWD variants of the sequence. FIG. 11 demonstrates this using a PIV5 sequence and antibody, while FIG. 6C (RLuc-N fusions labeled with *) shows the same approach for Nipah virus sequence and antibody.

Example 9

This Example provides a non-limiting demonstration that modified VLPs of this disclosure deliver the recombinant foreign protein to target cells. The panel shows successful delivery of luciferase using PIV5 VLPs that have both the PIV5 attachment (HN) and PIV5 fusion (F) viral glycoproteins. The control data are notable in that the VLPs have HN but not F, and in that case no luciferase was detected. Without intending to be constrained by any particular theory, it is considered this proves that in the Luciferase positive cases, the luciferase was not derived from VLPs that only bound to the target cells, but the luciferase was not introduced into the cells because if that did occur the same result would also be produced by the no F control. Thus, the data show that washing steps to remove residual attached VLPs were sufficient, and the assay results are only from luciferase signal produced by luciferase that was actually delivered from the VLPs to the cells.

It will be recognized from the foregoing Examples and description that we have defined regions near the C-terminal ends of paramyxovirus NP proteins that direct their virus assembly functions. A 15 residue DLD-containing sequence derived from the C-terminal end of PIV5 NP protein was capable of directing a foreign protein (*Renilla* luciferase) into PIV5 VLPs. Likewise, a 10 residue DLD-containing sequence derived from the C-terminal end of Nipah virus N protein was sufficient to direct *Renilla* luciferase into Nipah VLPs. Other paramyxoviruses harbor similar DLD-like sequences near their C-terminal ends as well (illustrated in FIG. 7). For example, the hPIV2 NP protein contains DFD directly in place of the DLD found in PIV5. NDV and HRSV N proteins have DND sequences near the C-terminal ends. Measles virus N protein contains the sequence DRDLLD (SEQ ID NO:13) at the C-terminal end, and alterations that affect this sequence have been found to disrupt virus assembly functions. The C-terminal portion of Sendai virus NP protein has also been implicated in virus assembly. The mumps virus NP protein harbors DWD in place of the DLD sequence found in PIV5 NP. We found this DWD sequence to be important for efficient mumps VLP production. Interestingly, DWD and DLD sequences did not function equivalently for VLP production, but rather were the key determinants that defined compatibilities between PIV5 and mumps virus M/NP protein pairs. Mumps VLP production was efficient only in the presence of DWD-containing NP proteins, such as wt mumps NP protein or PIV5 NP L507W that was engineered to contain DWD in place of DLD. Mumps VLP production was poor in the presence of DLD-containing NP proteins, such as wt PIV5 NP protein and mumps NP W547L that was engineered to contain DLD in place of DWD. Based on these collective findings, and without intending to be constrained by any particular theory, it is considered that paramyxoviruses share an overall common strategy for directing M-NP interactions, but with variations, controlled by DLD-like sequences, that play roles in defining M/NP compatibilities.

The ability to manipulate viral M-NP protein interactions supports use of VLP-based protein delivery tools. Under this scenario, foreign proteins of interest are tagged to induce their interaction with M protein and subsequent incorporation into fusion-competent VLPs, which would then deliver the contents to target cells. Although incorporation of target proteins into VLPs has been demonstrated in the past, the approaches used typically require direct fusion of the target protein amino acid sequence to the viral Gag or M protein that directs particle budding (Capul A A, de la Torre J C. 2008. A cell-based luciferase assay amenable to high-throughput screening of inhibitors of arenavirus budding. Virology 382:107-114; Kaczmarczyk S J, Sitaraman K, Young H A, Hughes S H, Chatterjee D K. 2011. Protein delivery using engineered virus-like particles. Proc. Natl. Acad. Sci. USA 108:16998-17003; Wolf M C, Wang Y, Freiberg A N, Aguilar H C, Holbrook M R, Lee B. 2009. A catalytically and genetically optimized beta-lactamase-matrix based assay for sensitive, specific, and higher throughput analysis of native henipavirus entry characteristics. Virol J 6:119). Here, we have instead achieved efficient incorporation of a foreign protein into paramyxovirus VLPs by harnessing the M-NP protein interactions that normally direct viral RNPs into budding virions. This approach is highly flexible, as it requires no modification at all to the viral matrix protein component, and the target protein in this case was modified only through addition of a 15-amino acid NP-derived binding sequence to its C-terminal end. The disclosure includes modification of this approach to include the paramyxovirus fusion and attachment glycoproteins to result in particles capable of transmitting the foreign proteins to target cells, similar to the "infectious" paramyxovirus VLPs that have been studied in the past and that are capable of delivering their NP-encapsidated minigenome cargos.

While the disclosure has been particularly shown and described with reference to specific embodiments, it should be understood by those having skill in the art that various changes in form and detail may be made therein without departing from the spirit and scope of the present disclosure as disclosed herein.

What is claimed is:

1. A paramyxovirus virus like particle (VLP) comprising a contiguous recombinant polypeptide comprising i) from 10-120 amino acids of a C-terminal domain of a paramyxovirus nucleocapsid (N) protein, and ii) a polypeptide sequence of a distinct protein that is a transcription factor, and wherein the transcription factor comprises a nuclear transport signal.

2. The VLP of claim 1, wherein the segment of the C-terminal domain is from a paramyxovirus that is one of PIV5, hPIV2, Nipah virus, Hendra virus, mumps virus (MuV), measles virus (MeV), Newcastle disease virus (NDV), Sendai virus (SeV), respiratory syncytial virus (RSV), and human metapneumovirus (hMPV).

3. The VLP of claim 1, wherein the VLP is present in a composition.

4. The VLP of claim 3, wherein the composition comprises a pharmaceutically acceptable carrier.

5. An expression vector encoding the recombinant polypeptide of the VLP of claim 1.

* * * * *

SEQUENCE LISTING

```
<160> NUMBER OF SEQ ID NOS: 14

<210> SEQ ID NO 1
<211> LENGTH: 23
<212> TYPE: PRT
<213> ORGANISM: PIV5 virus

<400> SEQUENCE: 1

Gln Asn Ala Ala Val Gly Ala Pro Ile His Thr Asp Asp Leu Asn Ala
1               5                   10                  15

Ala Leu Gly Asp Leu Asp Ile
            20


<210> SEQ ID NO 2
<211> LENGTH: 23
<212> TYPE: PRT
<213> ORGANISM: Mumps virus

<400> SEQUENCE: 2

Glu His Gly Asn Thr Phe Pro Asn Asn Pro Asn Gln Asn Ala Gln Ser
1               5                   10                  15

Gln Val Gly Asp Trp Asp Glu
            20


<210> SEQ ID NO 3
<211> LENGTH: 23
<212> TYPE: PRT
<213> ORGANISM: hPIV2 virus

<400> SEQUENCE: 3

Asp Asp Asp Ala Asn Asp Ala Thr Asp Gly Asn Asp Ile Ser Leu Glu
1               5                   10                  15

Leu Val Gly Asp Phe Asp Ser
            20


<210> SEQ ID NO 4
<211> LENGTH: 23
<212> TYPE: PRT
<213> ORGANISM: NiV virus

<400> SEQUENCE: 4

Ser Glu Lys Lys Asn Asn Gln Asp Leu Lys Pro Ala Gln Asn Asp Leu
1               5                   10                  15

Asp Phe Val Arg Ala Asp Val
            20


<210> SEQ ID NO 5
<211> LENGTH: 23
<212> TYPE: PRT
<213> ORGANISM: NDV virus

<400> SEQUENCE: 5

Gly Thr Pro Gln Ser Gly Pro Pro Pro Thr Pro Gly Pro Ser Gln Asp
1               5                   10                  15

Asn Asp Thr Asp Trp Gly Tyr
            20


<210> SEQ ID NO 6
<211> LENGTH: 23
<212> TYPE: PRT
<213> ORGANISM: SeV virus

<400> SEQUENCE: 6
```

-continued

Gly Arg Asn Asn Gly Val Asp His Asp Glu Asp Asp Asp Thr Ala Ala
1               5                   10                  15

Val Ala Gly Val Gly Gly Ile
            20

<210> SEQ ID NO 7
<211> LENGTH: 23
<212> TYPE: PRT
<213> ORGANISM: MeV virus

<400> SEQUENCE: 7

Gly Ile Leu Glu Glu Gln Gly Ser Asp Thr Asp Thr Pro Arg Val Tyr
1               5                   10                  15

Asn Asp Arg Asp Leu Leu Asp
            20

<210> SEQ ID NO 8
<211> LENGTH: 23
<212> TYPE: PRT
<213> ORGANISM: HRSV virus

<400> SEQUENCE: 8

Asp Leu Thr Ala Glu Glu Leu Glu Ala Ile Lys His Gln Leu Asn Pro
1               5                   10                  15

Lys Asp Asn Asp Val Glu Leu
            20

<210> SEQ ID NO 9
<211> LENGTH: 15
<212> TYPE: PRT
<213> ORGANISM: PIV5 virus

<400> SEQUENCE: 9

Ile His Thr Asp Asp Leu Asn Ala Ala Leu Gly Asp Leu Asp Ile
1               5                   10                  15

<210> SEQ ID NO 10
<211> LENGTH: 15
<212> TYPE: PRT
<213> ORGANISM: artificial sequence
<220> FEATURE:
<223> OTHER INFORMATION: modified viral N protein C terminus

<400> SEQUENCE: 10

Ile His Thr Asp Asp Leu Asn Ala Ala Leu Gly Asp Trp Asp Ile
1               5                   10                  15

<210> SEQ ID NO 11
<211> LENGTH: 12
<212> TYPE: PRT
<213> ORGANISM: artificial sequence
<220> FEATURE:
<223> OTHER INFORMATION: c-myc tag

<400> SEQUENCE: 11

Asn Glu Gln Lys Leu Ile Ser Glu Glu Asp Leu Cys
1               5                   10

<210> SEQ ID NO 12
<211> LENGTH: 6
<212> TYPE: PRT
<213> ORGANISM: Nipha virus

<400> SEQUENCE: 12

-continued

```
Asn Asp Leu Asp Phe Val
1               5


<210> SEQ ID NO 13
<211> LENGTH: 6
<212> TYPE: PRT
<213> ORGANISM: Measels virus

<400> SEQUENCE: 13

Asp Arg Asp Leu Leu Asp
1               5


<210> SEQ ID NO 14
<211> LENGTH: 15
<212> TYPE: PRT
<213> ORGANISM: artificial sequence
<220> FEATURE:
<223> OTHER INFORMATION: recombinant protein

<400> SEQUENCE: 14

Leu Lys Pro Ala Gln Asn Asp Leu Asp Phe Val Arg Ala Asp Val
1               5                   10                  15
```